US011690696B2

(12) United States Patent
Trulson et al.

(10) Patent No.: US 11,690,696 B2
(45) Date of Patent: *Jul. 4, 2023

(54) SYSTEMS AND METHODS FOR OPTOGENETIC IMAGING

(71) Applicant: INSCOPIX, INC., Mountain View, CA (US)

(72) Inventors: Mark O. Trulson, San Jose, CA (US); Alice Stamatakis, Mountain View, CA (US); Koen Visscher, Tucson, AZ (US)

(73) Assignee: INSCOPIX, INC., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/484,791

(22) Filed: Sep. 24, 2021

(65) Prior Publication Data
US 2022/0104907 A1    Apr. 7, 2022

Related U.S. Application Data

(63) Continuation of application No. 16/851,678, filed on Apr. 17, 2020, now Pat. No. 11,197,735, which is a (Continued)

(51) Int. Cl.
*A61B 90/20* (2016.01)
*G01N 21/64* (2006.01)
(Continued)

(52) U.S. Cl.
CPC ............ *A61B 90/20* (2016.02); *A61B 5/0059* (2013.01); *A61B 5/0071* (2013.01);
(Continued)

(58) Field of Classification Search
None
See application file for complete search history.

(56) References Cited

U.S. PATENT DOCUMENTS

| | | | |
|---|---|---|---|
| 5,736,410 | A | 4/1998 | Zarling et al. |
| 6,072,622 | A | 6/2000 | Biber et al. |

(Continued)

FOREIGN PATENT DOCUMENTS

| | | | |
|---|---|---|---|
| CN | 1668913 | A | 9/2005 |
| CN | 101116023 | A | 1/2008 |

(Continued)

OTHER PUBLICATIONS

Co-pending U.S. Appl. No. 15/331,549, inventors Trulson; Mark O. et al., filed Oct. 21, 2016.

(Continued)

*Primary Examiner* — Eileen M Adams
(74) *Attorney, Agent, or Firm* — Quarles & Brady LLP; Yakov S. Sidorin

(57) ABSTRACT

Provided herein are systems and methods for simultaneous imaging and stimulation using a microscope system. The microscope system can have a relatively small size compared to an average microscope system. The microscope can comprise in part an imaging light source and a stimulation light source. Light from the imaging light source and the stimulation light source can be spectrally separated to reduce cross talk between the stimulation light and the imaging light.

20 Claims, 19 Drawing Sheets

Related U.S. Application Data continuation of application No. 15/964,832, filed on Apr. 27, 2018, now Pat. No. 10,682,197, which is a continuation of application No. PCT/US2016/060717, filed on Nov. 4, 2016.

(60) Provisional application No. 62/383,122, filed on Sep. 2, 2016, provisional application No. 62/251,501, filed on Nov. 5, 2015.

(51) Int. Cl.
| | |
|---|---|
| *G02B 21/16* | (2006.01) |
| *G02B 21/06* | (2006.01) |
| *A61B 5/00* | (2006.01) |
| *G02B 21/02* | (2006.01) |
| *G02B 21/00* | (2006.01) |
| *G02B 21/32* | (2006.01) |
| *G02B 3/14* | (2006.01) |
| *A61B 5/24* | (2021.01) |
| *G01Q 10/00* | (2010.01) |
| *G02B 21/24* | (2006.01) |

(52) U.S. Cl.
CPC ....... *A61B 5/4064* (2013.01); *G01N 21/6458* (2013.01); *G02B 21/0004* (2013.01); *G02B 21/0096* (2013.01); *G02B 21/025* (2013.01); *G02B 21/06* (2013.01); *G02B 21/16* (2013.01); *G02B 21/32* (2013.01); *A61B 5/0035* (2013.01); *A61B 5/24* (2021.01); *G01N 2021/6439* (2013.01); *G01N 2021/6441* (2013.01); *G01Q 10/00* (2013.01); *G02B 3/14* (2013.01); *G02B 21/242* (2013.01)

(56) References Cited

U.S. PATENT DOCUMENTS

| | | |
|---|---|---|
| 7,511,891 B2 | 3/2009 | Messerschmidt |
| 8,346,346 B1 | 1/2013 | Schnitzer et al. |
| 8,624,967 B2 | 1/2014 | O'Connell et al. |
| 8,696,722 B2 | 4/2014 | Lee et al. |
| 8,788,021 B1 | 7/2014 | Flusberg et al. |
| 9,161,694 B2 | 10/2015 | Schnitzer et al. |
| 9,195,043 B2 | 11/2015 | Ghosh et al. |
| 9,474,448 B2 | 10/2016 | Ghosh et al. |
| 9,498,135 B2 | 11/2016 | Ghosh et al. |
| 9,629,554 B2 | 4/2017 | Ghosh et al. |
| 9,636,020 B2 | 5/2017 | Flusberg et al. |
| 9,839,361 B2 | 12/2017 | Schnitzer et al. |
| 10,200,657 B2 | 2/2019 | Ghosh |
| 10,386,623 B2 | 8/2019 | Visscher et al. |
| 10,682,197 B2 | 6/2020 | Trulson et al. |
| 10,813,552 B2 | 10/2020 | Ghosh et al. |
| 10,908,405 B2 | 2/2021 | Trulson et al. |
| 2004/0184660 A1* | 9/2004 | Treado .................. G06V 40/13 382/254 |
| 2005/0094260 A1 | 5/2005 | Tokuda et al. |
| 2006/0210962 A1 | 9/2006 | Imaizumi et al. |
| 2007/0109634 A1 | 5/2007 | Araki et al. |
| 2007/0253057 A1 | 11/2007 | Potsaid et al. |
| 2009/0201577 A1 | 8/2009 | Laplante et al. |
| 2010/0309547 A1 | 12/2010 | Hirata et al. |
| 2011/0127405 A1* | 6/2011 | Grossman .............. G02B 21/16 250/492.1 |
| 2011/0242649 A1 | 10/2011 | Murayama |
| 2011/0282331 A1 | 11/2011 | Brennan et al. |
| 2012/0062723 A1 | 3/2012 | Ghosh et al. |
| 2012/0105949 A1 | 5/2012 | Cummings et al. |
| 2012/0281211 A1 | 11/2012 | Murugkar et al. |
| 2013/0260382 A1* | 10/2013 | Ghosh .................... G02B 21/33 435/6.12 |
| 2014/0043462 A1 | 2/2014 | Ghosh et al. |
| 2014/0046408 A1 | 2/2014 | Shoham et al. |
| 2015/0087902 A1 | 3/2015 | Mertz et al. |
| 2015/0116812 A1 | 4/2015 | Matsumoto et al. |
| 2015/0148615 A1 | 5/2015 | Brennan et al. |
| 2015/0309295 A1 | 10/2015 | Cocker et al. |
| 2016/0022148 A1 | 1/2016 | Schnitzer et al. |
| 2016/0183782 A1* | 6/2016 | Yu .......................... A61B 90/20 606/4 |
| 2018/0136446 A1 | 5/2018 | Werley et al. |
| 2018/0177401 A1 | 6/2018 | Yang et al. |
| 2018/0217364 A1 | 8/2018 | Cocker et al. |
| 2018/0220106 A1 | 8/2018 | Ghosh |
| 2018/0296074 A1 | 10/2018 | Trulson et al. |
| 2018/0303573 A1 | 10/2018 | Trulson et al. |
| 2019/0133449 A1 | 5/2019 | Flusberg et al. |
| 2019/0133453 A1 | 5/2019 | Schnitzer et al. |
| 2019/0356884 A1 | 11/2019 | Ghosh |
| 2020/0057290 A1 | 2/2020 | Visscher et al. |
| 2021/0029329 A1 | 1/2021 | Ghosh |
| 2021/0059578 A1 | 3/2021 | Nassi et al. |
| 2021/0059782 A1 | 3/2021 | Trulson et al. |
| 2021/0141204 A1 | 5/2021 | Visscher et al. |
| 2021/0247603 A1 | 8/2021 | Trulson et al. |

FOREIGN PATENT DOCUMENTS

| | | |
|---|---|---|
| CN | 102003936 A | 4/2011 |
| CN | 102540446 A | 7/2012 |
| CN | 103097809 A | 5/2013 |
| CN | 103513411 A | 1/2014 |
| JP | 2001183524 A | 7/2001 |
| JP | 2001238229 A | 8/2001 |
| JP | 2005173487 A | 6/2005 |
| JP | 2005321753 A | 11/2005 |
| JP | 2006091506 A | 4/2006 |
| JP | 2006154230 A | 6/2006 |
| JP | 4125609 B2 | 7/2008 |
| JP | 2009175486 A | 8/2009 |
| JP | 2009528577 A | 8/2009 |
| JP | 2013545116 A | 12/2013 |
| WO | WO-9202839 A1 | 2/1992 |
| WO | WO-9729709 A1 | 8/1997 |
| WO | WO-2012026379 A1 | 3/2012 |
| WO | WO-2013157606 A1 | 10/2013 |
| WO | WO-2013172085 A1 | 11/2013 |
| WO | WO-2014057774 A1 | 4/2014 |
| WO | WO-2014071390 A1 | 5/2014 |
| WO | WO-2015087824 A1 | 6/2015 |

OTHER PUBLICATIONS

Co-pending U.S. Appl. No. 15/403,819, inventor Ghosh; Kunal, filed Jan. 11, 2017.
Co-pending U.S. Appl. No. 15/443,999, inventors Flusberg; Benjamin A. et al., filed Feb. 27, 2017.
Co-pending U.S. Appl. No. 15/727,317, inventors Flusberg; Benjamin A. et al., filed Oct. 6, 2017.
Co-pending U.S. Appl. No. 15/830,894, inventors Schnitzer; Mark J. et al., filed Dec. 4, 2017.
Co-pending U.S. Appl. No. 17/080,295, inventors Ghosh; Kunal et al., filed Oct. 26, 2020.
Co-pending U.S. Appl. No. 17/316,394, inventor Ghoshkunal, filed May 10, 2021.
Co-pending U.S. Appl. No. 17/481,123, inventors Visscherkoen et al., filed Sep. 21, 2021.
EP16843147.6 European Search Report dated Jun. 17, 2019.
EP16843147.6 European Search Report dated Mar. 8, 2019.
EP16863123.2 European Examination report dated Feb. 20, 2020.
EP16863123.2 Extended European Search Report dated Apr. 25, 2019.
Erdogan, T., Optical filters for wavelength selection in fluorescence instrumentation. Current Protocols in Cytometry, Apr. 1, 2011; pp. 2.4.1-2.4.25.
Grintech. High-NA Endomicroscopic Imaging Objective now available as achromatic version. Rev. Dec. 2013. 1 page.
International Search Report and Written Opinion dated Jan. 13, 2017 for International PCT Patent Application No. PCT/US2016/050277.

(56) References Cited

OTHER PUBLICATIONS

International Search Report and Written Opinion dated Jan. 19, 2017 for International PCT Patent Application No. PCT/US2016/060717.
Leigh, et al. Multi-color miniature dual-axis confocal microscope for point-of-care pathology. Opt Lett. Jun. 15, 2012;37(12):2430-2. doi: 10.1364/OL.37.002430.
Liu Riu et al., Extendable, miniaturized multi-modal optical imaging system: cortical hemodynamic observation in freely moving animals. Optics Express, Jan. 28, 2013, vol. 21, No. 2, pp. 1911-1924.
Martin, Paul R. Rheinberg Illumination: A Fresh Approach to High Magnification Color Contrast. Aug. 26, 2014. Available at https://www.mccrone.com/mm/rheinberg-illumination-a-fresh-approach-to-high-magnification-color-contrast.
Murari, et al., An integrated imaging microscope for untethered cortical imaging in freely-moving animals. EIEE in medicine and biology, 2010; 5795-5798.
Murari, et al., Design and characterization of a miniaturized Epi-illuminated microscope. EIEE in medicine and biology, 2009; 5369-5372.
Pellett, et al. Two-color STED microscopy in living cells. Biomed Opt Express. Aug. 1, 2011;2(8):2364-71. doi: 10.1364/BOE.2.002364. Epub Jul. 22, 2011.
U.S. Appl. No. 16/851,678 Notice of Allowance dated Aug. 12, 2021.
U.S. Appl. No. 15/256,296 Notice of Allowance dated Oct. 6, 2020.
U.S. Appl. No. 15/256,296 Office Action dated Apr. 3, 2020.
U.S. Appl. No. 15/256,296 Office Action dated Feb. 15, 2019.
U.S. Appl. No. 15/256,296 Office Action dated Nov. 18, 2019.
U.S. Appl. No. 15/964,832 Office Action dated Feb. 27, 2020.
U.S. Appl. No. 15/964,832 Office Action dated Sep. 9, 2019.
U.S. Appl. No. 16/851,678 Office Action dated May 4, 2021.

\* cited by examiner

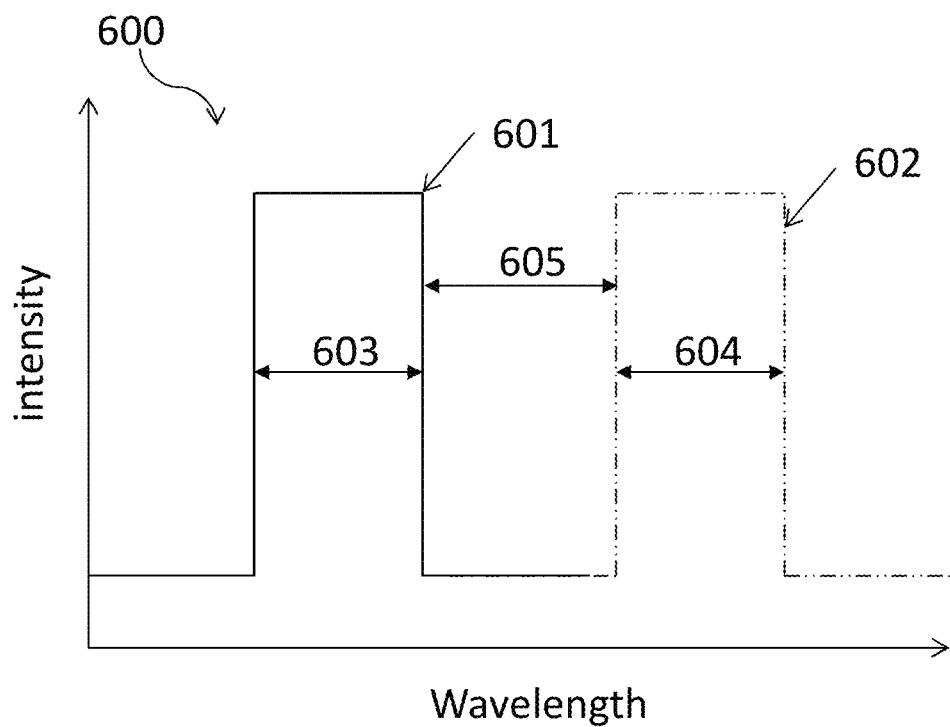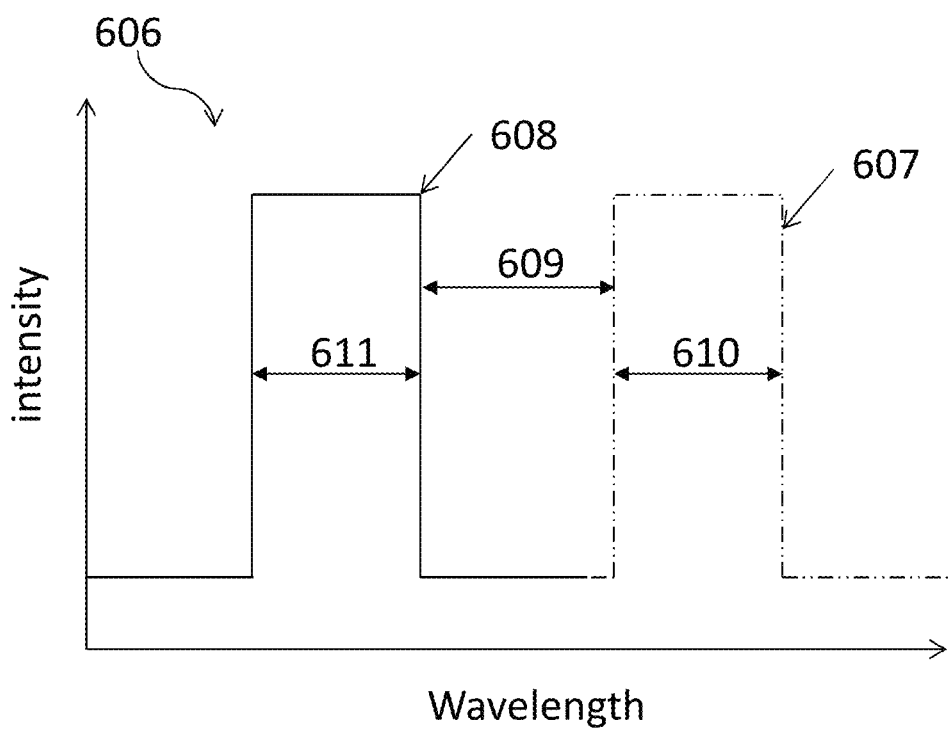
FIG. 6

455 EX-LED
590 OG-LED

560 EX-LED
455 OG-LED

EX-LED = LED for excitation of calcium indicator
OG-LED = LED for activation of opsin

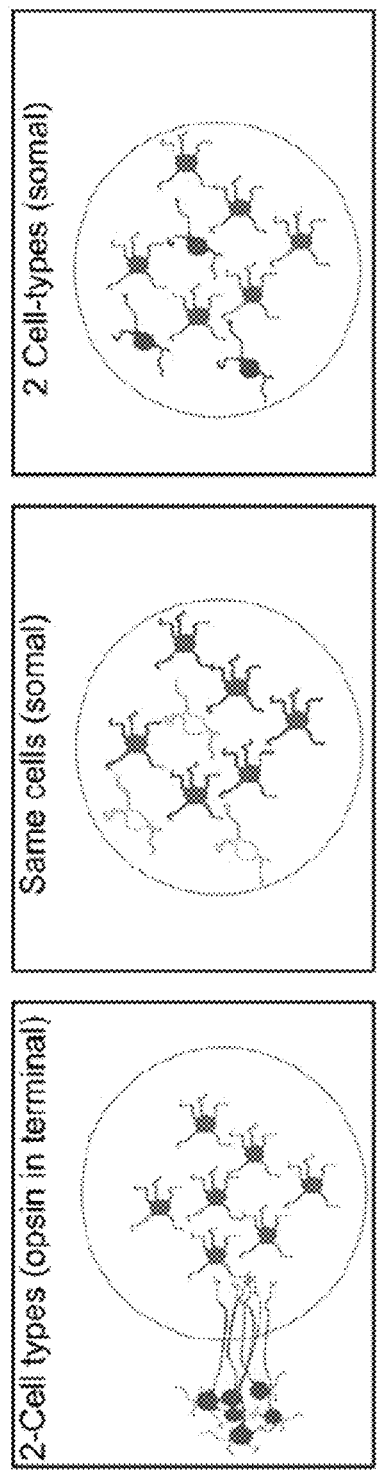

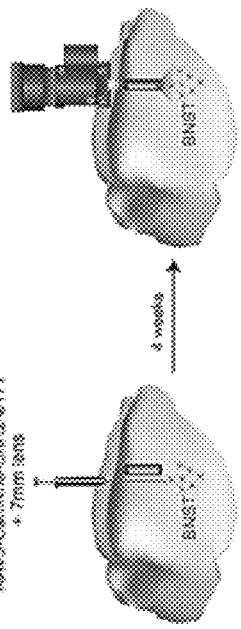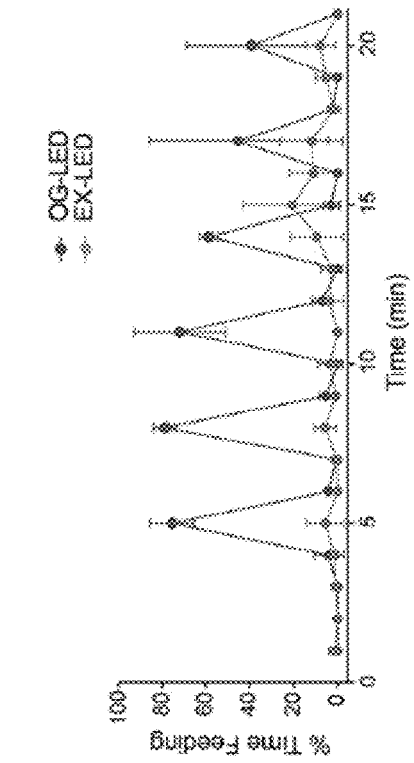
FIG. 12A
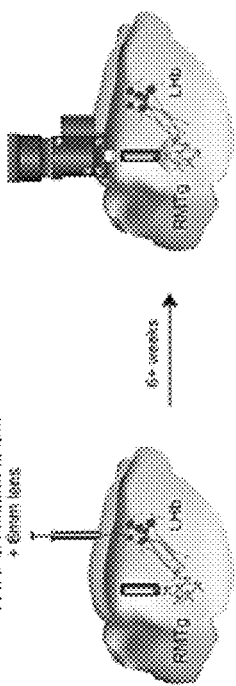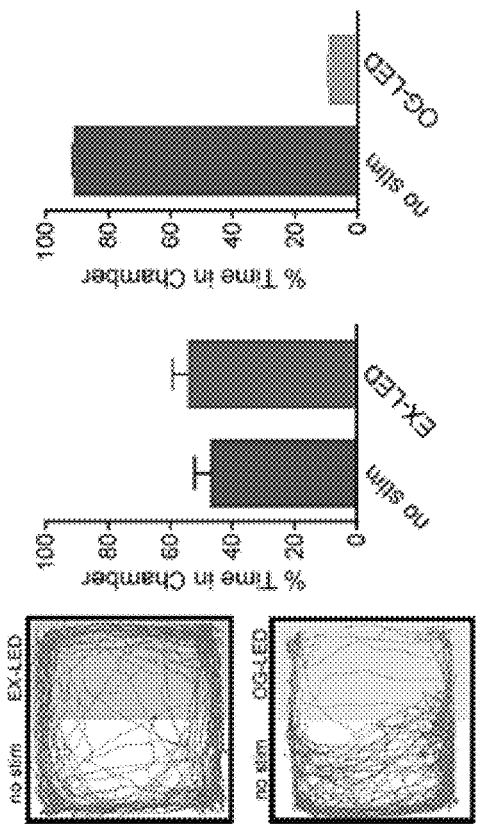
FIG. 12B

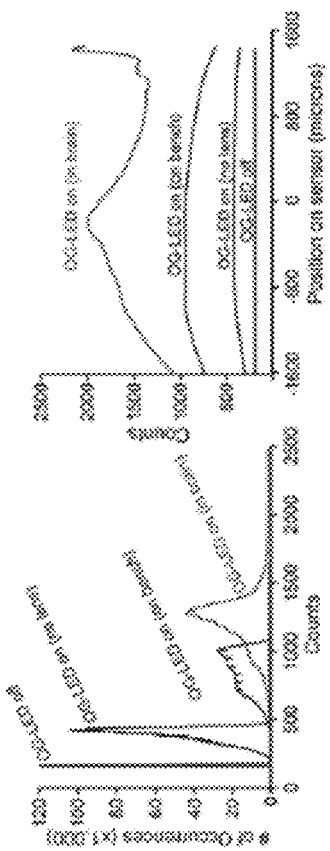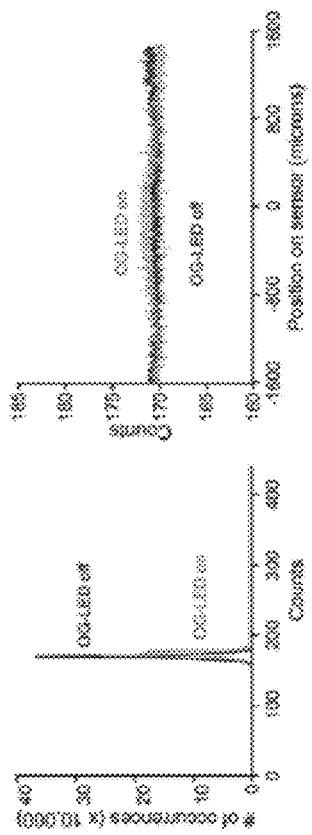
FIG. 13A
FIG. 13B

SYSTEMS AND METHODS FOR OPTOGENETIC IMAGING

CROSS-REFERENCE

This application is a continuation of U.S. application Ser. No. 16/851,678, filed Apr. 17, 2020, which is a continuation of U.S. application Ser. No. 15/964,832, filed Apr. 27, 2018, which is a continuation of International Application No. PCT/US2016/060717, filed Nov. 4, 2016, which claims the benefit of U.S. Provisional Application No. 62/251,501, filed on Nov. 5, 2015, and U.S. Provisional Application No. 62/383,122, filed on Sep. 2, 2016, each of which is entirely incorporated herein by reference.

BACKGROUND

Biological samples can be stimulated by light energy. Stimulation can initiate, enhance, and/or inhibit one or more activities performed by a portion of the biological sample stimulated by the light energy. In some cases, nerve cells can be activated or deactivated by light energy. One or more populations of nerve cells can communicate signals based on activation by light energy. Biological samples can have small spatial scales such that they may comprise one or more features, such as cells, that are not visible to a human eye. Microscopes can be employed to visualize the small features of biological samples.

SUMMARY

Provided herein are systems and methods for simultaneously imaging a magnified sample and stimulating at least a fraction of the sample. The imaging and stimulation can be performed with a microscope system. The microscope system can include a small microscope with a total volume of less than one cubic inch. The microscope can comprise a stimulation light source and an imaging light source. The stimulation light source can be incident on a smaller area than an area on which the imaging light is incident. The microscope system can deliver imaging light at a relatively lower intensity compared to the stimulation light. The wave properties (e.g., wavelength, frequency, intensity, and power) of the imaging light and the stimulation light can be modulated to reduce cross talk between the imaging and stimulation light.

Thus, in one aspect, a microscope system for simultaneous imaging and stimulation is provided. The system comprises: an imaging light directing arrangement that directs imaging light from an imaging light source to a sample in a field-of-view of the microscope system; a stimulation light directing arrangement that directs stimulation light from a stimulation light source to at least a portion of the sample for stimulation of the portion of the sample while the sample is illuminated by the imaging light from the imaging directing arrangement; an optical path that directs the imaging light and the stimulation light to the sample, wherein the imaging light and the stimulation light are transmitted through at least one shared optical element in the optical path and wherein the stimulation light overlaps the imaging light at the sample; and an image sensor that receives emitted light from the sample to generate an image of the sample while stimulation light is directed to the portion of the sample for stimulation of the portion of the sample.

In some embodiments, the stimulation light source comprises (1) a single stimulation light source that is patterned by a spatial light modulator, or (2) a plurality of stimulation light sources. In some embodiments, (1) the patterned stimulation light is spatially or temporally modulated, or (2) wherein at least a fraction of the plurality of stimulation light sources are turned on when the stimulation light directing arrangement directs stimulation light to the portion of the sample. In some embodiments, (1) the patterned stimulation light is spatially or temporally modulated based on a command to direct stimulation light to a specified portion of the sample, or (2) wherein the fraction of the plurality of stimulation light sources that are turned on is based on a command to direct stimulation light to a specified portion of the sample. In some embodiments, the patterned stimulation light or the plurality of stimulation light sources are controlled by a computer system that performs image analysis on an image generated by the image sensor. In some embodiments, image analysis determines a location of one or more objects of interest in the sample. In some embodiments, the imaging light and the stimulation light are delivered to the sample through a same optical path. In some embodiments, the same optical path that directs the imaging light and the stimulation light to the sample comprises an optical probe that (1) facilitates delivery of the imaging light and the stimulation light to the sample, and (2) facilitates relay of the sample's image to the image sensor. In some embodiments, the computer system controls an illumination pattern of the stimulation light source with the aid of one or more processors based on the image analysis on the image generated by the image sensor. In some embodiments, the microscope has a volume of about 1 cubic inch. In some embodiments, the microscope is mounted on a freely moving organism. In some embodiments, the sample comprises brain tissue. In some embodiments, a power density of the stimulation light is at least 10× a power density of the imaging light. In some embodiments, a wavelength range of the stimulation light is spectrally separated from a wavelength range of the imaging light by at least 10 nm. In some embodiments, the image sensor that receives emitted light from the sample generates an image of the sample with a spatial resolution of at least 50 µm or better. In some embodiments, the imaging light directing arrangement is in optical communication with a light source that is off board the microscope system. In some embodiments, the stimulation light directing arrangement is in optical communication with a light source that is off board the microscope system.

In another aspect, a method for simultaneous imaging and stimulating a sample with a microscope is provided. The method comprises: directing imaging light with aid of an imaging light directing arrangement that directs imaging light from an imaging light source to at least a portion of the sample in a field-of-view of the microscope, wherein the imaging light has a wavelength within an ultraviolet, visible, or near infrared wavelength spectrum; generating an image of the sample with aid of an image sensor of the microscope that receives emitted light from the sample to generate the image of the sample; and directing stimulation light with aid of a stimulation light directing arrangement that directs stimulation light from a stimulation light source to the portion of the sample for stimulation of the portion of the sample while the sample is illuminated by the imaging light from the imaging directing arrangement.

In some embodiments, the stimulation light source comprises a single light source that is patterned by a spatial light modulator or wherein the stimulation light source comprises a plurality of spatially distinct stimulation light sources. In some embodiments, the method further comprises (1) temporally or spatially modulating the patterned stimulation light source, or (2) turning on at least a fraction of the plurality of stimulation light sources to direct the stimulation light to the portion of the sample. In some embodiments, the patterned stimulation light source is spatially or temporally modulated based on a command to direct stimulation light to a specified portion of the sample, or wherein the fraction of the plurality of stimulation light sources that are turned on is based on a command to direct stimulation light to a specified portion of the sample. In some embodiments, the method further comprises analyzing the image of the sample by one or more processors of a computer system and controlling the patterned stimulation light source or the plurality of stimulation light sources based on analysis of the image of the sample. In some embodiments, the analysis of the image includes determining a location of one or more objects of interest in the sample. In some embodiments, the imaging light and the stimulation light are delivered to the sample through a same optical path. In some embodiments, the same optical path that simultaneously directs the imaging light and the stimulation light to the sample comprises an optical probe that (1) facilitates delivery of the imaging light and the stimulation light to the sample, and (2) facilitates relay of the object's image to the image sensor. In some embodiments, the microscope has a volume of about 1 cubic inch. In some embodiments, the microscope is mounted on a freely moving organism. In some embodiments, the sample comprises brain tissue. In some embodiments, a power density of the stimulation light is at least 10× a power density of the imaging light. In some embodiments, a wavelength range of the stimulation light is spectrally separated from a wavelength range of the imaging light by at least 10 nm. In some embodiments, the image sensor that receives emitted light from the sample generates an image of the sample with a spatial resolution of at least 20 µm.

In another aspect, a microscope system for simultaneous imaging and stimulation is provided. The system comprises: an imaging light directing arrangement that directs imaging light from an imaging light source to a sample in a field-of-view of the microscope system; a stimulation light directing arrangement that directs stimulation light from a stimulation light source to a different portion of the sample outside of the field-of-view for stimulation of the different portion of the sample while the sample is illuminated by the imaging light from the imaging directing arrangement; and an image sensor that receives emitted light from the sample to generate an image of the sample while stimulation light is directed to the different portion of the sample for stimulation of the different portion of the sample.

In some embodiments, the stimulation light source comprises (1) a single stimulation light source that is patterned by a spatial light modulator, or (2) a plurality of stimulation light sources. In some embodiments, (1) the patterned stimulation light is spatially or temporally modulated, or (2) wherein at least a fraction of the plurality of stimulation light sources are turned on when the stimulation light directing arrangement directs stimulation light to the different portion of the sample. In some embodiments, (1) the patterned stimulation light is spatially or temporally modulated based on a command to direct stimulation light to a specified portion of the sample, or (2) wherein the fraction of the plurality of stimulation light sources that are turned on is based on a command to direct stimulation light to a specified portion of the sample. In some embodiments, the patterned stimulation light or the plurality of stimulation light sources are controlled by a computer system that performs image analysis on an image generated by the image sensor. In some embodiments, image analysis determines a location of one or more objects of interest in the sample. In some embodiments, the imaging light and the stimulation light are delivered to the sample through different optical paths. In some embodiments, at least one of the optical paths comprises an optical probe that (1) facilitates delivery of the imaging light or the stimulation light to the sample, and (2) facilitates relay of the sample's image to the image sensor. In some embodiments, the computer system controls an illumination pattern of the stimulation light source with the aid of one or more processors based on the image analysis on the image generated by the image sensor. In some embodiments, the microscope has a volume of about 1 cubic inch. In some embodiments, the microscope is mounted on a freely moving organism. In some embodiments, the sample comprises brain tissue. In some embodiments, a power density of the stimulation light is at least 10× a power density of the imaging light. In some embodiments, a wavelength range of the stimulation light is spectrally separated from a wavelength range of the imaging light by at least 10 nm. In some embodiments, wherein the image sensor that receives emitted light from the sample generates an image of the sample with a spatial resolution of at least 50 µm or better. In some embodiments, the imaging light directing arrangement is in optical communication with a light source that is off board the microscope system. In some embodiments, the stimulation light directing arrangement is in optical communication with a light source that is off board the microscope system. In some embodiments, the field-of-view is an imaging field-of-view. In some embodiments, the stimulation light does not overlap the imaging light at the sample.

Disclosed herein are optical systems for simultaneous imaging and stimulation of tissue within a subject, the system comprising: a) an optical assembly comprising: i) an imaging light source comprising one or more light-emitting elements and configured to direct imaging light to tissue within a specified field-of-view; ii) a stimulation light source comprising one or more light-emitting elements and configured to direct stimulation light to tissue within at least a portion of said field-of-view; iii) an optical path that directs the imaging light and the stimulation light to the tissue, wherein the imaging light and the stimulation light are transmitted to the tissue through at least one shared deformable lens; and iv) an image sensor configured to receive light that is reflected, scattered, or emitted by the tissue to generate an image of the tissue within said field-of-view; and b) a baseplate, wherein the baseplate is configured to be mounted on the subject in a fixed position and to receive the optical assembly, thereby aligning the optical assembly relative to the tissue of the subject upon attachment to the baseplate, and wherein the optical assembly is removable from the baseplate.

In some embodiments, the field-of-view is about 1 mm×1 mm. In some embodiments, the focal plane of said image is adjustable over a range of about 300 µm without loss of spatial resolution. In some embodiments, the optical assembly is capable of generating images over a tissue volume of about 1 mm×1 mm×300 um. In some embodiments, the optical assembly is capable of generating images with a spatial resolution of better than 2 µm at the center of the field-of-view. In some embodiments, the optical assembly further comprises one or more corrective optical elements and is capable of generating images with a spatial resolution of better than 2 µm over the entire field-of-view. In some embodiments, the optical assembly further comprises at least a second deformable lens. In some embodiments, the focal plane of said image is the same as the focal plane for stimulation light generated by said stimulation light source. In some embodiments, the focal plane of said image is different from the focal plane for stimulation light generated by said stimulation light source. In some embodiments, the at least one deformable lens is selected from the group consisting of liquid lenses, liquid crystal lenses, and piezo-actuated tunable lenses, or any combination thereof. In some embodiments, the at least one shared deformable lens is positioned in close proximity to a gradient index (GRIN) objective lens. In some embodiments, the at least one shared deformable lens is positioned in close proximity to the end of the gradient index (GRIN) objective lens that is farthest from the tissue. In some embodiments, the optical assembly further comprises a probe that may be partially implanted in the tissue. In some embodiments, the tissue-to-image sensor path length is less than about 5 cm. In some embodiments, the tissue-to-imaging light source path length is less than about 5 cm. In some embodiments, the imaging light source comprises two or more light-emitting elements, and is configured to direct imaging light of two or more different wavelengths to the tissue with the specified field-of-view. In some embodiments, the stimulation light source comprises two or more light-emitting elements, and is configured to direct stimulation light of two or more different wavelengths to the tissue within at least a portion of said field-of-view. In some embodiments, the stimulation light source is configured to direct stimulation light to the tissue in a user-defined spatial pattern. In some embodiments, the user-defined spatial pattern has a spatial resolution of better than 5 µm at the focal plane. In some embodiments, the optical system further comprises a processor and a memory device, wherein the processor is configured to execute a series of software-encoded instructions stored in the memory device. In some embodiments, the software-encoded instructions include instructions for: (i) modulating the imaging light intensity in a time-dependent or spatially-dependent manner, (ii) modulating the stimulation light intensity in a time-dependent or spatially-dependent manner, (iii) varying the focal depth in a time-dependent manner, and (iv) capturing one or more images of the tissue within the specified field-of-view at specified times, or any combination thereof. In some embodiments, the tissue is brain tissue, and the software-encoded instructions comprise instructions for modulating the stimulation light in a time-dependent or spatially-dependent manner to induce a neurological response in said brain tissue. In some embodiments, the total volume of the system is less than about 5 cm$^3$. In some embodiments, the total weight of the system is less than about 4 grams. In some embodiments, the system comprises at least a second optical assembly that may be mounted on the same baseplate. In some embodiments, the one or more light-emitting elements of the imaging light source or the stimulation light source comprise optical fibers that are coupled to one or more external light sources. In some embodiments, the system is mounted by means of said baseplate on a freely mobile subject. In some embodiments, the subject is selected from the group consisting of mice, rats, cats, dogs, pigs, cows, horses, monkeys, chimpanzees, orangutans, gorillas, and humans. In some embodiments, the system is used for preclinical research. In some embodiments, the system is used for clinical research. In some embodiments, the system is used to determine a clinical diagnostic test result. In some embodiments, the system is used to direct stimulation light to the tissue in a time-modulated or spatially-modulated manner that produces a therapeutic effect.

Disclosed herein are optical systems for simultaneous imaging and stimulation of tissue within a subject, the system comprising: an optical imaging probe comprising an imaging light source and an image sensor, and configured to receive light that is reflected, scattered, or emitted by the tissue to generate an image of the tissue within a specified field-of-view; an optical stimulation probe comprising one or more light-emitting elements and configured to direct stimulation light to tissue within said field-of-view, to tissue outside said field-of-view, or to any combination thereof; and a baseplate, wherein the baseplate is configured to be mounted on the subject in a fixed position and to receive the optical imaging and stimulation probes, thereby aligning the optical imaging and stimulation probes relative to the tissue of the subject upon attachment to the baseplate, and wherein the optical imaging and stimulation probes are removable from the baseplate.

In some embodiments, the optical system further comprises at least second optical imaging probe, at least a second optical stimulation probe, or any combination thereof attached to the same baseplate, and wherein the configuration of the baseplate determines the lateral distance between the optical imaging and optical stimulation probes. In some embodiments, the optical imaging probe(s) and optical stimulation probe(s) each comprise at least one deformable lens that permits adjustment of the focal plane over a range of about 300 µm without loss of spatial resolution. In some embodiments, the field-of-view of the optical imaging probe is about 1 mm×1 mm. In some embodiments, the optical imaging probe is capable of generating images over a tissue volume of about 1 mm×1 mm×300 um. In some embodiments, the optical imaging probe is capable of generating images with a spatial resolution of better than 2 µm at the center of the field-of-view. In some embodiments, the optical imaging probe further comprises one or more corrective optical elements and is capable of generating images with a spatial resolution of better than 2 µm over the entire field-of-view. In some embodiments, the focal plane of said image is the same as the focal plane for stimulation light generated by said optical stimulation probe. In some embodiments, the focal plane of said image is different from the focal plane for stimulation light generated by said optical stimulation probe. In some embodiments, the at least one deformable lens is selected from the group consisting of liquid lenses, liquid crystal lenses, and piezo-actuated tunable lenses, or any combination thereof. In some embodiments, the at least one deformable lens of the optical imaging probe is positioned in close proximity to a gradient index (GRIN) objective lens. In some embodiments, the at least one deformable lens is positioned in close proximity to the end of the gradient index (GRIN) objective lens that is farthest from the tissue. In some embodiments, the optical imaging probe may be partially implanted in the tissue. In some embodiments, the optical stimulation probe may be partially implanted in the tissue. In some embodiments, the tissue-to-image sensor path length of the optical imaging probe is less than about 5 cm. In some embodiments, the tissue-to-imaging light source path length of the optical stimulation probe is less than about 5 cm. In some embodiments, the imaging light source comprises two or more light-emitting elements, and is configured to direct imaging light of two or more different wavelengths to the tissue with the specified field-of-view. In some embodiments, the optical stimulation probe comprises two or more light-emitting elements configured to direct stimulation light of two or more different wavelengths to the tissue within said field-of-view, to tissue outside said field-of-view, or to any combination thereof. In some embodiments, the optical stimulation probe is configured to direct stimulation light to the tissue in a user-defined spatial pattern. In some embodiments, the user-defined pattern has a spatial resolution of better than 5 µm at the focal plane. In some embodiments, the optical system further comprises a processor and a memory device, wherein the processor is configured to execute a series of software-encoded instructions stored in the memory device. In some embodiments, the software-encoded instructions include instructions for: (i) modulating the imaging light intensity in a time-dependent or spatially-dependent manner, (ii) modulating the stimulation light intensity in a time-dependent or spatially-dependent manner, (iii) varying the focal depth in a time-dependent manner, and (iv) capturing one or more images of the tissue within the specified field-of-view at specified times, or any combination thereof. In some embodiments, the tissue is brain tissue, and the software-encoded instructions comprise instructions for modulating the stimulation light in a time-dependent or spatially-dependent manner to induce a neurological response in said brain tissue. In some embodiments, the total volume of the system is less than about 5 cm$^3$. In some embodiments, the total weight of the system is less than about 4 grams. In some embodiments, the imaging light source or the one or more light-emitting elements of the optical stimulation probe comprise optical fibers that are coupled to one or more external light sources. In some embodiments, the system is mounted by means of said baseplate on a freely mobile subject. In some embodiments, the subject is selected from the group consisting of mice, rats, cats, dogs, pigs, cows, horses, monkeys, chimpanzees, orangutans, gorillas, and humans. In some embodiments, the system is used for preclinical research. In some embodiments, the system is used for clinical research. In some embodiments, the system is used to determine a clinical diagnostic test result. In some embodiments, the system is used to direct stimulation light to the tissue in a time-modulated or spatially-modulated manner that produces a therapeutic effect.

Disclosed herein are optical systems for simultaneous imaging and stimulation of tissue within a subject, the system comprising: an optical assembly comprising: an optical imaging probe comprising an imaging light source and an image sensor, and configured to receive light that is reflected, scattered, or emitted by the tissue to generate an image of the tissue within a specified field-of-view; and an optical stimulation probe comprising one or more light-emitting elements and configured to direct stimulation light to tissue within said field-of-view, to tissue outside of said field-of-view, or to any combination thereof; and a baseplate, wherein the baseplate is configured to be mounted on the subject in a fixed position and to receive the optical assembly, thereby aligning the optical assembly relative to the tissue of the subject upon attachment to the baseplate, and wherein the optical assembly has a total volume of less than about 5 cm$^3$ and is removable from the baseplate.

Also disclosed herein are optical systems for simultaneous imaging and stimulation of tissue within a subject, the system comprising: an optical assembly comprising: an optical imaging probe comprising an imaging light source, a deformable lens, and an image sensor, and configured to receive light that is reflected, scattered, or emitted by the tissue to generate a series of tomographic images of the tissue within a field-of-view of about 1 mm×1 mm over a depth of about 300 μm; and an optical stimulation probe comprising one or more light-emitting elements and configured to direct stimulation light to tissue within said field-of-view, to tissue outside of said field-of-view, or to any combination thereof; and a baseplate, wherein the baseplate is configured to be mounted on the subject in a fixed position and to receive the optical assembly, thereby aligning the optical assembly relative to the tissue of the subject upon attachment to the baseplate, and wherein the optical assembly has a total volume of less than about 5 cm$^3$ and is removable from the baseplate.

In some embodiments, imaging light produced by the imaging light source and stimulation light are transmitted to the tissue through at least one shared deformable lens that permits adjustment of the focal plane over a range of about 300 μm without loss of spatial resolution. In some embodiments, the field-of-view of the optical imaging probe is about 1 mm×1 mm. In some embodiments, the optical imaging probe is capable of generating images over a tissue volume of about 1 mm×1 mm×300 um. In some embodiments, the optical imaging probe is capable of generating images with a spatial resolution of better than 2 μm at the center of the field-of-view. In some embodiments, the optical imaging probe further comprises one or more corrective optical elements and is capable of generating images with a spatial resolution of better than 2 μm over the entire field-of-view. In some embodiments, the focal plane of said image is the same as the focal plane for stimulation light generated by said optical stimulation probe. In some embodiments, the focal plane of said image is different from the focal plane for stimulation light generated by said optical stimulation probe. In some embodiments, the at least one deformable lens is selected from the group consisting of liquid lenses, liquid crystal lenses, and piezo-actuated tunable lenses, or any combination thereof. In some embodiments, the at least one deformable lens of the optical imaging probe is positioned in close proximity to a gradient index (GRIN) objective lens. In some embodiments, the at least one deformable lens is positioned in close proximity to the end of the gradient index (GRIN) objective lens that is farthest from the tissue. In some embodiments, the optical imaging probe may be partially implanted in the tissue. In some embodiments, the optical stimulation probe may be partially implanted in the tissue. In some embodiments, the tissue-to-image sensor path length of the optical imaging probe is less than about 5 cm. In some embodiments, the tissue-to-imaging light source path length of the optical stimulation probe is less than about 5 cm. In some embodiments, the imaging light source comprises two or more light-emitting elements, and is configured to direct imaging light of two or more different peak wavelengths to the tissue with the specified field-of-view. In some embodiments, the optical stimulation probe comprises two or more light-emitting elements configured to direct stimulation light of two or more different peak wavelengths to the tissue within said field-of-view, to tissue outside said field-of-view, or to any combination thereof. In some embodiments, the optical stimulation probe is configured to direct stimulation light to the tissue in a user-defined spatial pattern. In some embodiments, the user-defined spatial pattern has a spatial resolution of better than 5 μm at the focal plane. In some embodiments, the optical system further comprises a processor and a memory device, wherein the processor is configured to execute a series of software-encoded instructions stored in the memory device. In some embodiments, the software-encoded instructions include instructions for: (i) modulating the imaging light intensity in a time-dependent or spatially-dependent manner, (ii) modulating the stimulation light intensity in a time-dependent or spatially-dependent manner, (iii) varying the focal depth in a time-dependent manner, and (iv) capturing one or more images of the tissue within the specified field-of-view at specified times, or any combination thereof. In some embodiments, the tissue is brain tissue, and wherein the software-encoded instructions comprise instructions for modulating the stimulation light in a time-dependent or spatially-dependent manner to induce a neurological response in said brain tissue. In some embodiments, the total volume of the system is less than about 5 cm³. In some embodiments, the total weight of the system is less than about 4 grams. In some embodiments, the imaging light source or the one or more light-emitting elements of the optical stimulation probe comprise optical fibers that are coupled to one or more external light sources. In some embodiments, the system is mounted by means of said baseplate on a freely mobile subject. In some embodiments, the subject is selected from the group consisting of mice, rats, cats, dogs, pigs, cows, horses, monkeys, chimpanzees, orangutans, gorillas, and humans. In some embodiments, the system is used for preclinical research. In some embodiments, the system is used for clinical research. In some embodiments, the system is used to determine a clinical diagnostic test result. In some embodiments, the system is used to direct stimulation light to the tissue in a time-modulated or spatially-modulated manner that produces a therapeutic effect.

Disclosed herein are optical systems for simultaneous imaging and stimulation of tissue within a subject, the system comprising: an optical assembly comprising: an illumination optical path comprising one or more light-emitting elements and configured to direct imaging light to tissue within a specified field-of-view; a stimulation optical path comprising one or more light-emitting elements and configured to direct stimulation light to tissue within said field-of-view, to tissue outside of said field-of-view, or to any combination thereof; an imaging optical path comprising one or more image sensors and configured to receive light reflected, scattered, or emitted by the tissue to generate an image of the tissue within said field-of-view; and a baseplate, wherein the baseplate is configured to be mounted on the subject in a fixed position and to receive the optical assembly, thereby aligning the optical assembly relative to the tissue of the subject upon attachment to the baseplate, and wherein the optical assembly is removable from the baseplate.

Disclosed herein are optical systems for simultaneous imaging and stimulation of tissue within a subject, the system comprising: a) an optical assembly comprising: an illumination optical path comprising one or more light-emitting elements and configured to direct imaging light to tissue within a specified field-of-view; a stimulation optical path comprising one or more light-emitting elements and configured to direct stimulation light to tissue within said field-of-view, to tissue outside of said field-of-view, or to any combination thereof; an imaging optical path comprising one or more image sensors and configured to receive light reflected, scattered, or emitted by the tissue to generate an image of the tissue within said field-of-view; a wireless adapter configured to provide wireless communication of information or power between the optical assembly and an external controller; and a housing configured to enclose the optical assembly and wireless adapter, wherein the housing is hermetically-sealed and comprises a biocompatible outer surface; wherein the optical system is partially- or fully-implantable within the tissue of the subject.

In some embodiments, the specified field-of-view is of about 1 mm×1 mm. In some embodiments, the optical assembly is configured to acquire images with a spatial resolution of better than about 2 µm at the center of the field-of-view. In some embodiments, the optical assembly is configured to acquire images with a spatial resolution of better than about 2 µm over the entire field-of-view by means of adding one or more corrective optical elements to the optical assembly. In some embodiments, the optical assembly further comprises one or more deformable lenses configured to adjust the focal depth of the imaging optical path, the stimulation optical path, or both. In some embodiments, the one or more deformable lenses are configured to adjust the focal depth of the imaging optical path, the stimulation optical path, or both, over a range of about 300 µm without loss of spatial resolution. In some embodiments, the one or more deformable lenses are selected from the group consisting of liquid lenses, liquid crystal lenses, and piezo-actuated tunable lenses, or any combination thereof. In some embodiments, the one or more deformable lenses are configured so that the imaging optical path and the stimulation optical path direct light to the same focal plane. In some embodiments, the optical assembly is configured to acquire images over a tissue volume of about 1 mm×1 mm×300 um. In some embodiments, the stimulation optical path is further configured to direct the stimulation light to the tissue in a user-defined spatial pattern. In some embodiments, the user-defined spatial pattern has a spatial resolution of better than about 5 µm at the focal plane. In some embodiments, the optical system further comprises a first processor and a memory device, wherein the processor is configured to execute a series of software-encoded instructions stored in the memory device. In some embodiments, the software-encoded instructions include instructions for: (i) modulating the imaging light intensity in a time-dependent or spatially-dependent manner, (ii) modulating the stimulation light intensity in a time-dependent or spatially-dependent manner, (iii) varying the focal depth in a time-dependent manner, and (iv) capturing one or more images of the tissue within the specified field-of-view at specified times, or any combination thereof. In some embodiments, the tissue is brain tissue, and the software-encoded instructions comprise instructions for modulating the stimulation light in a time-dependent or spatially-dependent manner to induce a neurological response in said brain tissue. In some embodiments, the total volume of the system is less than about 5 cm³. In some embodiments, the total weight of the system is less than about 4 grams. In some embodiments, the system comprises at least a second illumination optical path, at least a second stimulation optical path, at least a second imaging optical path, or any combination thereof. In some embodiments, the one or more light-emitting elements of the illumination optical path or the stimulation optical path comprise optical fibers that are coupled to one or more external light sources. In some embodiments, the baseplate is configured to allow attachment of two or more optical assemblies. In some embodiments, the wireless adapter is configured to provide wireless communication via a radio frequency or optical link. In some embodiments, the wireless adapter is configured to enable wireless read and write operations separately or simultaneously. In some embodiments, the system is mounted on, partially implanted within, or fully-implanted within a freely mobile subject. In some embodiments, the subject is selected from the group consisting of mice, rats, cats, dogs, pigs, cows, horses, monkeys, chimpanzees, orangutans, gorillas, and humans. In some embodiments, the system is used for preclinical research. In some embodiments, the system is used for clinical research. In some embodiments, the system is used to determine a clinical diagnostic test result. In some embodiments, the system is used to direct stimulation light to the tissue in a time-modulated or spatially-modulated manner that produces a therapeutic effect.

Disclosed herein are methods for simultaneous stimulation and imaging of tissue within a subject, the method comprising: providing an optical system according to any one of the embodiments disclosed herein; providing a subject comprising the tissue to be stimulated and imaged; mounting or implanting the optical system of step (a) on or within the subject; and generating one or more images of the tissue before, during, or after directing stimulation light to the tissue of said subject in a time-modulated or spatially-modulated manner.

In some embodiments, the subject is selected from the group consisting of mice, rats, cats, dogs, pigs, cows, horses, monkeys, chimpanzees, orangutans, gorillas, and humans. In some embodiments, the method is performed as part of preclinical research. In some embodiments, the method is performed as part of clinical research. In some embodiments, the method further comprises determining a clinical diagnostic test result. In some embodiments, the method further comprises directing stimulation light to the tissue in a time-modulated or spatially-modulated manner that produces a therapeutic effect.

Disclosed herein are microscope systems for simultaneous imaging and stimulation of tissue within a subject, the microscope system comprising: an optical assembly comprising: an illumination optical path comprising one or more light-emitting elements and configured to direct imaging light to tissue within a specified field-of-view; a stimulation optical path comprising one or more light-emitting elements and configured to direct stimulation light to tissue within said field-of-view, to tissue outside of said field-of-view, or to tissue partially within said field-of-view; an imaging optical path comprising one or more image sensors and configured to receive light reflected, scattered, or emitted by the tissue to generate an image of the tissue within said field-of-view; and a baseplate, wherein the baseplate is configured to be mounted on the subject in a fixed position and to receive the optical assembly, thereby aligning the optical assembly relative to the tissue of the subject upon attachment to the baseplate, and wherein the optical assembly is removable from the baseplate.

In some embodiments, the specified field-of-view is about 1 mm×1 mm. In some embodiments, the specified field-of-view is about 2 mm×2 mm. In some embodiments, the specified field-of-view is about 4 mm×4 mm. In some embodiments, the imaging light is fluorescence excitation light. In some embodiments, the fluorescence excitation light is provided within a wavelength range of 400 nm to 500 nm, and the stimulation light is provided within a wavelength range of 500 nm and 800 nm. In some embodiments, the fluorescence excitation light is provided within a wavelength range of 500 nm to 650 nm, and the stimulation light is provided within a wavelength range of 350 nm and 560 nm. In some embodiments, the optical assembly is configured to acquire images with a spatial resolution of better than about 2 μm at the center of the field-of-view. In some embodiments, the optical assembly is configured to acquire images with a spatial resolution of better than about 2 μm over the entire field-of-view by means of adding one or more corrective optical elements to the optical assembly. In some embodiments, the optical assembly further comprises one or more deformable lenses configured to adjust the focal depth of the imaging optical path, the stimulation optical path, or both. In some embodiments, the illumination optical path, stimulation optical path, and imaging optical path share at least one deformable lens. In some embodiments, the one or more deformable lenses are configured to adjust the focal depth of the imaging optical path, the stimulation optical path, or both, over a range of about 300 μm without loss of spatial resolution. In some embodiments, the one or more deformable lenses are selected from the group consisting of liquid lenses, liquid crystal lenses, and piezo-actuated tunable lenses, or any combination thereof. In some embodiments, the one or more deformable lenses are configured so that the imaging optical path and the stimulation optical path direct light to the same focal plane. In some embodiments, the optical assembly is configured to acquire images over a tissue volume of about 1 mm×1 mm×300 um. In some embodiments, the stimulation optical path is further configured to direct the stimulation light to the tissue in a user-defined spatial pattern. In some embodiments, the user-defined spatial pattern has a spatial resolution of better than about 5 μm at the focal plane. In some embodiments, the microscope system further comprises a first processor and a memory device, wherein the processor is configured to execute a series of software-encoded instructions stored in the memory device. In some embodiments, the software-encoded instructions include instructions for: (i) modulating the imaging light intensity in a time-dependent or spatially-dependent manner, (ii) modulating the stimulation light intensity in a time-dependent or spatially-dependent manner, (iii) varying the focal depth in a time-dependent manner, and (iv) capturing one or more images of the tissue within the specified field-of-view at specified times, or any combination thereof. In some embodiments, the tissue is brain tissue, and wherein the software-encoded instructions comprise instructions for modulating the stimulation light in a time-dependent or spatially-dependent manner to induce a neurological response in said brain tissue. In some embodiments, the total volume of the system is less than about 5 cm$^3$. In some embodiments, the total weight of the system is less than about 4 grams. In some embodiments, the illumination and imaging optical paths are packaged in a first housing as an optical imaging probe. In some embodiments, the stimulation optical path is packaged in a second housing as an optical stimulation probe. In some embodiments, the system comprises at least a second optical imaging probe, at least a second optical stimulation probe, or any combination thereof, attached to the baseplate. In some embodiments, the one or more light-emitting elements of the illumination optical path or the stimulation optical path comprise optical fibers that are coupled to one or more external light sources. In some embodiments, the system is mounted on or partially implanted within a freely mobile subject. In some embodiments, the illumination optical path, the stimulation optical path, and the imaging optical path further comprise a shared endoscopic probe that is partially implanted in the tissue of the subject. In some embodiments, the subject is selected from the group consisting of mice, rats, cats, dogs, pigs, cows, horses, monkeys, chimpanzees, orangutans, gorillas, and humans. In some embodiments, the system is used for preclinical research. In some embodiments, the system is used for clinical research. In some embodiments, the system is used to determine a clinical diagnostic test result. In some embodiments, the system is used for photostimulation of neuronal tissue of the central nervous system, peripheral nervous system, or both. In some embodiments, the system is used to direct stimulation light to the tissue in a time-modulated or spatially-modulated manner that produces a therapeutic effect.

Disclosed herein are methods for simultaneous stimulation and imaging of tissue within a subject, the method comprising: providing a microscope system described in the embodiments above wherein the system is used to direct stimulation light to the tissue in a time-modulated or spatially-modulated manner that produces a therapeutic effect; providing a subject comprising the tissue to be stimulated and imaged; mounting or implanting the microscope system of step (a) on or within the subject; and generating one or more images of the tissue before, during, or after directing stimulation light to the tissue of said subject in a time-modulated or spatially-modulated manner.

In some embodiments, the subject is selected from the group consisting of mice, rats, cats, dogs, pigs, cows, horses, monkeys, chimpanzees, orangutans, gorillas, and humans. In some embodiments, the method is performed as part of preclinical research. In some embodiments, the method is performed as part of clinical research. In some embodiments, the method further comprises determining a clinical diagnostic test result. In some embodiments, method further comprises directing stimulation light to the tissue in a time-modulated or spatially-modulated manner that produces a therapeutic effect.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference in their entirety to the same extent as if each individual publication, patent, or patent application was specifically and individually indicated to be incorporated by reference in its entirety. In the event of a conflict between a term herein and a term in an incorporated reference, the term herein controls.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

FIG. 6 shows possible emission spectra as a function of wavelength for the imaging and stimulation light source.

FIG. 8A: 455 nm excitation LED, 590 nm activation LED. FIG. 8B: 560 nm excitation LED, 455 nm activation LED.

FIGS. 9A-C illustrate non-limiting examples of different imaging applications for a compact optogenetics microscope system.

FIGS. 12A-B show examples of data for in vivo characterization of biological crosstalk.

FIGS. 13A-B show examples of data for in vivo characterization of optical crosstalk.

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Provided herein are systems and methods for operation of a microscope system, also referred to herein as an optical system and/or an optogenetic microscope system. The microscope system may be configured to provide concurrent manipulation and observation of a sample. The sample can be a biological sample. At least a portion of the sample can comprise one or more objects of interest, for example, cells. In some cases, the sample can comprise neuronal populations. At least a portion of the sample that includes one or more objects of interest can be activated or deactivated by light stimulation from a microscope system. The stimulation light can stimulate light-activated ion channels (e.g., opsins) in a cellular membrane (this process may also be referred to as "optogenetic stimulation" or "optogenetic modulation"). The opsins can occur in the cellular membrane naturally. In some cases, the opsins can be loaded into the cellular membrane by a genetic modification of the cell that causes the cell membrane to incorporate opsins. Opsin generating genes can be introduced into the cell through virus mediated transfection. The microscope system can simultaneously image the sample (e.g., using fluorescence) while providing stimulation light to the sample. Simultaneous imaging and stimulation can permit a user to observe one or more portions of the sample (e.g., cells, neurons, or neuronal populations) that are stimulated by the stimulation light. The sample can be simultaneously stimulated by stimulation light and imaged by imaging light with a single integrated optogenetic microscope system. The sample can be imaged optically, e.g., by collecting imaging light that is scattered, reflected, or transmitted by the sample, or by exciting fluorescence in the sample using an excitation imaging light source and collecting the emitted fluorescent light to form an image. The sample can be imaged by light provided directly to the sample. The sample can be imaged by light that is not transmitted through one or more boundaries such as skin or bone prior to being incident on the sample. In some embodiments, the disclosed optogenetic microscope systems further comprise a baseplate which may be mounted on or implanted at a fixed position on a freely mobile subject. The baseplate may be configured to receive the optogenetic microscope, thereby aligning the microscope relative to tissue of the subject upon attachment of the microscope to the baseplate, and also allows subsequent removal or replacement of the microscope.

Figure 1:
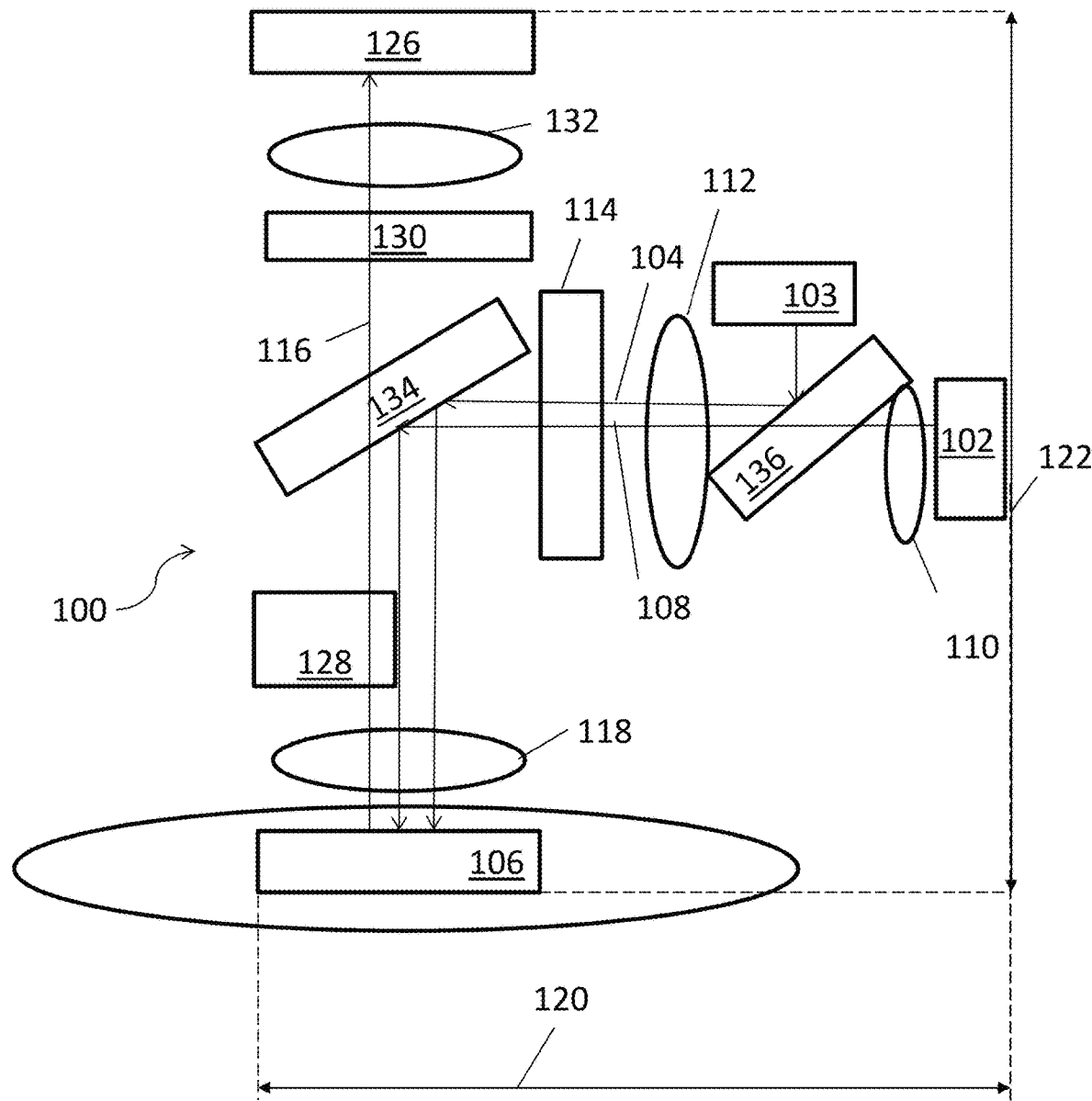
FIG. 1 shows a schematic of a small optogenetic microscope system.

The optogenetic microscope can be any microscope configured to deliver light to a sample from a first light source to generate an image of the sample and alternately or simultaneously deliver light to the sample from a second light source to stimulate at least a portion of the sample. Stimulation of the sample can comprise initiating an electrochemical signal from the sample. FIG. 1 shows a diagram of an optogenetic microscope system 100 configured to deliver imaging light and stimulation light to a sample. The microscope system 100 can deliver the imaging light and the stimulation light to the sample simultaneously. The microscope system can deliver the imaging light and the stimulation light to the sample at separate time periods.

The compact optogenetic microscope disclosed herein is one non-limiting example of an optical system. As used herein, an optical device or optical system may be any device or system that comprises one or more optical components, e.g., lenses, mirrors, optical filters, prisms, diffraction gratings, monochromators, and the like, that are arranged in a manner such that the device or system performs an optical function such as delivering light to a specified field-of-view, collecting light from a specified field-of-view and forming an image at a specified focal plane, providing a magnified image of a specified field-of-view, and the like. The arrangement of optical components in an optical device or optical system thus constitutes an "optical path" which functions to transfer light from one position in space to another. Thus one may refer, for example, to an "illumination optical path" used to deliver imaging light to the sample or tissue within a defined field-of-view", or to a "stimulation optical path" used to deliver stimulation light to the sample or tissue within a defined field-of-view, or to an "imaging optical path" used to deliver light collected from the sample or tissue within a defined field of view to the image sensor.

As used herein, an "optical assembly" may refer to a grouping of one or more optical components that comprise all or a portion of the optical components of an optical device or system, and may often further comprise electronic components, e.g., light sources or photodetectors, and mechanical components, e.g., mounts or fixtures, that hold the individual optical components in a fixed or adjustable orientation relative to each other and/or a fixed or adjustable distance relative to each other. In some instances, an optical device or system may comprise more than one optical assembly (or optical sub-system). In some instances, an optical device or system may comprise two or more optical assemblies wherein the two or more different optical assemblies are configured to perform the same or different functions. For example, an optical assembly (e.g., an illumination optical assembly, or "optical illumination probe") may comprise the optical and electronic components required to deliver imaging light to the sample within a defined field-of-view. Alternatively, an optical assembly (e.g., a stimulation optical assembly, or "optical stimulation probe") may comprise the optical components required to deliver photostimulation light to the sample within a defined field-of-view.

In another instance, an optical assembly (e.g., an imaging optical assembly, or "optical imaging probe") may comprise the optical and electronic components required to both deliver imaging light to the sample within a defined field-of-view, and collect light that is reflected, scattered, or emitted by the sample to capture an image of the sample with a defined field-of-view. Thus an optical system such as the optogenetic microscope systems disclosed herein may, in some embodiments, comprise one or more optical assemblies or optical probes in any combination to provide a variety of illumination, photostimulation, and imaging functionalities. In some embodiments, the disclosed optogenetic microscope systems may further comprise additional mechanical components, e.g., housings, baseplates, or position adjustment mechanisms, electromechanical components, e.g., manual or motorized translation stages or other micro-positioning devices, or electronic components, e.g., light sources, photodetectors, image sensors, light sources, temperature sensors, temperature control elements, temperature controllers, analogue-to-digital converters, digital-to-analogue converters, amplifiers, processors, memory devices, and the like.

The microscope system can comprise an imaging light directing arrangement 103 and a stimulation light directing arrangement 102. The imaging light directing arrangement and the stimulation light directing arrangement can be contained in a housing that contains at least a fraction of one or more optical components of the microscope system. The light directing arrangement may be optically isolated from ambient light. The imaging light directing arrangement can include an imaging light source. The imaging light source can be on-board the microscope. The imaging light source can generate imaging light. The imaging light directing arrangement can be in optical communication with an imaging light source that is off board the light directing arrangement. The imaging light source can be off board the microscope. The imaging light source may or may not be contained in the housing. The imaging light directing arrangement can be in optical communication with the imaging light source through an optical transmission element, for example a fiber optic element. The stimulation light directing arrangement can be in optical communication with stimulation light source that is off board the light directing arrangement. The stimulation light source can generate stimulation light. The stimulation light source can be on-board the microscope. The stimulation light source can be off board the microscope. The stimulation light source may or may not be contained in the housing. The stimulation light directing arrangement can be in optical communication with the stimulation light source through an optical transmission element, for example a fiber optic element.

The optogenetic microscope can image light from a sample at different wavelengths (e.g., colors) such that a user can study different cellular components and/or interactions. In some cases, different cell populations can be identified by imaging of different color fluorescent tags. The microscope can be configured to magnify one or more features of a sample such that a user can study components and/or interactions outside a size range detectable by a user's eyes. The light imaged from the sample at different wavelengths can correspond to different colors that can be imaged in a multi-color microscope imaging process. The microscope system can be configured to detect light of multiple colors simultaneously.

The optogenetic microscope can be configured to perform single-color or multi-color imaging. The optogenetic microscope can simultaneously stimulate a sample while imaging two or more different color (e.g., wavelength) emissions (e.g., fluorescence) from the sample. In some cases the two or more different colors can be from two more different dyes that have been added to the sample. The dyes can be fluorescent dyes. Cells with different proteins and/or different genetic markers and/or different neurological functions can be identified with different dyes. The two color imaging can aid in identifying an object of interest (e.g. cell population) for targeting of stimulation light from the optogenetic microscope.

Imaging multiple colors simultaneously can permit a user to image different samples, for example, different cellular populations and interactions between the different cellular populations. The different cellular populations can be stained with a color marker that can be detected by the microscope system. Alternatively, the different cellular populations can naturally emit different color markers that can be detected by the microscope system. In some cases, subpopulations within a population can be identified with multi-color microscopy by detecting a protein or genetic marker. Differences in the subpopulation can be studied and/or studied by stimulation by the stimulation light with the multi-color imaging. In some cases, imaging dynamic from one cellular population and hemodynamics can be studied to identify metabolic and/or blood-brain barrier phenomena (e.g., drug delivery).

In some cases, the optogenetic microscope can be configured to perform single-color imaging. The optogenetic microscope can simultaneously stimulate a sample while imaging a single color (e.g., wavelength or wavelength band) emission (e.g., fluorescence) from the sample. The optogenetic microscope can comprise a monochromatic image sensor that detects light from the sample within a visible range of wavelengths. The optogenetic microscope can comprise a monochromatic image sensor that detects light from the sample outside of a visible range of wavelengths. The optogenetic microscope can comprise a monochromatic image sensor that detects light from the sample outside of and within a visible range of wavelengths. In some embodiments, the optogenetic microscope can comprise more than one image sensor, e.g., two, three, four, or more image sensors.

The microscope system provided herein can be configured to provide real-time simultaneous imaging and stimulation of one or more portions of a living sample. Each portion of the living sample can comprise one or more objects of interest such as cells or cell populations. The living sample can be subjected to various stimuli while one or more objects of interest (e.g., cells) of the living sample are simultaneously imaged and stimulated. The living sample can be subjected to effects of a pharmaceutical prior to or during simultaneous imaging and stimulation by the microscope system. In some cases, the living sample can be an organ and/or tissue in an organism. The organism can be subjected to various stimuli while one or more objects of interest (e.g., cells) of the organism are simultaneously imaged and stimulated. In some cases, the stimuli can be chosen to cause stress, tranquility, agitation, and/or another predetermined biological response by the organism.

In some cases, the microscope system described herein can permit observation of interactions between a first group of cells and a second group of cells in a sample. At least one of the first group of cells and the second group of cells can be a population of neurons. In an example, a user can detect a first group of cells and a second group of cells in a sample by directing imaging light to the sample using imaging functionality of the microscope system. The user can then provide stimulation light to at least one of the first group of cells and the second group of cells using stimulation functionality of the microscope system. Stimulation and imaging light can be provided to the sample simultaneously such that the user can continue to observe the first group of cells and the second group of cells while at least one of the first group of cells and the second group of cells is stimulated. The user can observe activity patterns that occur between the first group of cells and the second group of cells when at least one of the first group of cells and the second group of cells is stimulated.

The imaging light source may comprise one or more LEDs, or other types of light emitting elements. The imaging light source can be a light-emitting-diode (LED) or an organic light-emitting-diode (OLED). Light from the imaging light source 104 can be directed to the sample 106 through an optical arrangement comprising one or more optical elements. The imaging light source may provide essentially monochromatic light. Alternatively the imaging light source may provide imaging light at multiple wavelengths. In one example, the imaging light source may comprise two or more LEDs (or other light emitting elements) that emit light at two or more different colors (e.g., wavelengths or wavelength ranges). The imaging light source may provide light for single-color or multi-color imaging that is directed by the illumination optical path to all, or a portion of the sample or tissue within the field-of-view of the disclosed optogenetic microscopes or optical probes. In some embodiments, the one or more light emitting elements of the imaging light source may comprise optical fibers that are optically and/or mechanically coupled to one or more external light sources.

The imaging light can be an excitation light source such that when light from the imaging light is incident on the sample, the sample emits fluorescence from one or more fluorophores contained in the sample. The fluorophores can occur naturally in the sample or they can be added to the sample. In some embodiments, any type of luminescence may be detected for imaging of the sample, including but not limited to photoluminescence (e.g., fluorescence, phosphorescence), chemiluminescence, bioluminescence, or electroluminescence. Multiple colors as a result of reflectance, luminescence, scattering, or other light interactions may be detected. In some cases, light from the imaging light source can be incident on the sample and at least a fraction of the light can be reflected by the sample. The reflected light can be detected to generate an image of the sample.

In some cases, the imaging light can provide imaging light to the sample with a power density of at most about 1000 $\mu W/mm^2$, 900 $\mu W/mm^2$, 800 $\mu W/mm^2$, 700 $\mu W/mm^2$, 600 $\mu W/mm^2$, 500 $\mu W/mm^2$, 550 $\mu W/mm^2$, 500 $\mu W/mm^2$, 450 $\mu W/mm^2$, 400 $\mu W/mm^2$, 350 $\mu W/mm^2$, 300 $\mu W/mm^2$, 250 $\mu W/mm^2$, 200 $\mu W/mm^2$, 150 $\mu W/mm^2$, 100 $\mu W/mm^2$, 75 $\mu W/mm^2$, 50 $\mu W/mm^2$, 25 $\mu W/mm^2$, 15 $\mu W/mm^2$, 10 $\mu W/mm^2$, 5 $\mu W/mm^2$, 1 $\mu W/mm^2$, 0.5 $\mu W/mm^2$, or 0.1 $\mu W/mm^2$. In some cases, the power density can be greater than 1000 $\mu W/mm^2$. The power density provided by the imaging light can fall between any of the values listed. Highest levels of imaging light may refer to the power density of the imaging light incident on the sample. Alternatively, higher levels of imaging light may refer to the power density of the imaging light incident on a surface of an optical element in a light path that direct imaging light to the sample. Highest levels of imaging light may also refer to power consumed by the imaging light source.

The microscope device can additionally comprise a stimulation light source. The stimulation light source can be a single light source or a plurality (e.g. two or more) light sources. The stimulation light source can comprise a plurality of lights sources arranged in rows and/or columns in a matrix of m×n light sources where m can be an integer from 1 to 1000 and n can be an integer from 1 to 1000. The plurality of light sources in the stimulation light source can be arranged in one or more columns. The plurality of light sources in the stimulation light source can be arranged in one or more rows. The plurality of light sources in the stimulation light source can be arranged in an irregular pattern. The plurality of light sources in the stimulation light source can be arranged in an array. The light sources can be light emitting diodes (LEDs). The light sources can be organic light emitting diodes (OLEDs). The light sources can be micro-LEDs. The light sources can be high-power LEDs. The light sources can be laser diodes. The light sources can be vertical-cavity surface-emitting lasers (VCSEL). The light sources can be any other light emitting elements. In some cases, the stimulation light source may comprise two or more light-emitting elements that emit light at two more different colors (e.g., wavelengths or wavelength ranges). In some cases, the high-power LEDs can emit light with a power of at least about 0.1 W, 0.25 W, 0.5 W, 0.75 W, 1 W, 2 W, 3 W, 4 W, 5 W, 10 W, 15 W, 20 W, or 25 W. The high-power LEDs can emit light at a greater power than the light emitted by the imaging light source.

This stimulation light source can generate stimulation light 108. The stimulation light can be directed to the sample 106 by an optical arrangement. The optical arrangement that directs stimulation light to the sample can include at least some of the same optical elements as the optical arrangement that directs imaging light to the sample. One or more optical elements of the optical arrangement that direct imaging light to the sample can be shared with the optical arrangement for directing stimulation light to the sample. Stimulation light and imaging light can be transmitted through the shared optical element simultaneously. In some cases, one or more of the optical elements can be a filter element. The filter can be a spectral filter configured to transmit light in a predetermined range of wavelengths. The same filter and/or different filters may be provided for the imaging and stimulation light. The different filters can be configured to transmit different discrete wavelengths and/or ranges of wavelengths. The different filters can be configured to transmit the same discrete wavelength and/or ranges of wavelengths.

In some cases, the stimulation light can be provided to the sample at a higher power density relative to the imaging light. The low level power density of the imaging light can reduce the probability that the imaging light will inadvertently stimulate a portion of the sample. The power density of the stimulation light can be at least about 1.5×, 2×, 3×, 4×, 5×, 6×, 7×, 8×, 9×, 10×, 20×, 30×, 40×, 50×, 60×, 70×, 80×, 90×, or 100× the power density of the imaging light.

The stimulation light from the stimulation light directing arrangement and the imaging light from the imaging light directing arrangement can be directed through a dichroic mirror 136. The stimulation light can be transmitted through a condenser lens 110 prior to being directed with the imaging light at the dichroic mirror. The condenser lens can be placed close to the stimulation light source. The condenser lens can be almost touching the stimulation light source. The condenser lens can contact the stimulation light source. A distance between the condenser lens and the stimulation light source can be at most about 0.001 mm, 0.005 mm, 0.01 mm, 0.05 mm, 0.1 mm, 0.5 mm, 1 mm, 5 mm, 10 mm, 20 mm, 30 mm, 40 mm, or 50 mm. The condenser lens can condense light from the stimulation light source into a light beam with a flat intensity profile (e.g., spatially uniform intensity). The condenser lens can collimate the stimulation light. The condenser lens can condense light from the stimulation light source into a light beam that has little or no variation in intensity across the beam area. In some cases, the variation of intensity across the beam area of the stimulation light after transmission through the condenser can be at most about 50%. In some cases, the intensity across the beam area of the stimulation light after transmission through the condenser can vary by at most about 25%. In some cases, the variability of intensity across the beam area of the stimulation light after transmission through the condenser can be at most about 10%. In some cases, the variability of intensity across the beam area of the stimulation light after transmission through the condenser can be at most about 5%. In some cases, the variability of intensity across the beam area of the stimulation light after transmission through the condenser can be at most about 1%. Providing a uniform beam of stimulation light can be important for generating uniform stimulation of the sample.

After being transmitted through the dichroic mirror 136 the stimulation light and the imaging light can be transmitted through a second condenser lens 112 and an excitation filter 114. The second condenser lens can increase the attenuation of light from the stimulation light source and/or the imaging light source to the sample. The second condenser lens can collect light from different angles and redirect this light into a collimated beam for delivery to the sample. Without the condenser lens, light traveling at some of these different angles may not remain in the optical path to be delivered to the sample. Without the condenser lens the irradiance of the imaging light source may need to be increased in order to provide sufficient light to the sample for imaging. Increasing the irradiance of the imaging light can increase the probability of undesirable stimulation of the sample with the imaging light.

A second dichroic element 134 can direct the stimulation and/or the imaging light to the sample.

Light from the sample, for example fluorescence emission and/or reflected light from the sample can be directed through an optical path to an image sensor 126 to generate a digital representation of the image of the sample. When light from the sample is emitted and/or reflected in two or more different wavelength ranges (e.g., colors) a chromatic aberration correction element 128 can be provided in the optical path between the sample and the image sensor. The chromatic aberration correction element can adjust the focal length of the light in one or more of the different wavelength ranges such that the focal points are substantially the same. The chromatic aberration correction element can adjust the focal length in one or more of the different wavelength ranges such that light in each of the different wavelength ranges is focused onto a light detector in the image sensor.

The optical path from the sample to the image sensor can also include an emission filter 130 and/or a tube lens 132. The emission filter can prevent light in one or more wavelength ranges from being transmitted to the image sensor. The emission filter can select light in one or more wavelength ranges to be transmitted to the image sensor. The tube lens can focus light from the sample on to the image sensor. The tube lens can correct spherical and chromatic aberrations.

The microscope system can be sized and shaped such that a living organism can wear the microscope system while the microscope system is performing imaging and stimulation of at least a portion of one or more tissues or organs of the organism. The microscope system can be sized and shaped such that typical motions and/or activities of the living organism are not impeded and/or altered by the microscope system when the microscope system is worn by or attached to the living organism. For example, the living organism may be freely moving while the microscope system is imaging and stimulating a tissue of the living organism. The living organism may be walking about while the microscope system is imaging and/or stimulating a tissue of the organism such as brain tissue.

In some cases the disclosed microscopes and optical systems (e.g., optical probes) can be a relatively small. The microscope or system can have a maximum dimension less than about 5 inches, 4 inches, 3 inches, 2 inches, 1 inch, or 0.5 inches. The microscope or system can have a maximum dimension less than about 12.7 cm, 10.2 cm, 7.6 cm, 5.1 cm, 2.5 cm, or 1.3 cm. A maximum dimension of the microscope or system may be any dimension of the microscope or system (e.g., length, width, height, diameter) that is greater than the other dimensions of the microscope. The microscope or system may have a volume of less than or equal to about 10 cubic inches, 7 cubic inches, 6 cubic inches, 5 cubic inches, 4 cubic inches, 3 cubic inches, 2.5 cubic inches, 2 cubic inches, 1.5 cubic inches, 1 cubic inch, 0.7 cubic inches, 0.5 cubic inches, 0.3 cubic inches, 0.1 cubic inch, 0.05 cubic inch, 0.01 cubic inch, 0.005 cubic inch, or 0.001 cubic inch. The microscope or system may have a volume of less than or equal to about 170 $cm^3$, 115 $cm^3$, 100 $cm^3$, 82 $cm^3$, 66 $cm^3$, 50 $cm^3$, 40 $cm^3$, 33 $cm^3$, 25 $cm^3$, 16 $cm^3$, 11 $cm^3$, 8 $cm^3$, 5 $cm^3$, 1.6 $cm^3$, 0.8 $cm^3$, 0.2 $cm^3$, or 0.02 $cm^3$. The microscope or system may have a lateral cross section (e.g., footprint) or less than or equal to about 5 square inches, 4 square inches, 3 square inches, 2 square inches, 1.5 square inches, 1.2 square inches, 1 square inch, 0.9 square inches, 0.8 square inches, 0.7 square inches, 0.6 square inches, 0.5 square inches, 0.3 square inches, 0.1 square inches, 0.05 square inches, 0.01 square inches, 0.005 square inches, or 0.001 square inches. The microscope or system may have a mass of less than or equal to about 10 grams, 7 grams, 5 grams, 4 grams, 3.5 grams, 3 grams, 2.5 grams, 2 grams, 1.5 grams, 1 gram, 0.5 grams, or 0.1 grams. The small dimensions may be useful for applications where a subject may be small, to provide reduced interference with activities of the subject by the microscope. A small lateral cross-section is useful when the subject is small and/or there is a limited space or area where the microscope or system may be mounted. A small lateral cross-section can permit many microscopes or optical probes to be mounted in a space with limited area. The small microscope or optical system may be capable of simultaneous stimulation and imaging as described herein. The small microscope or optical system may be advantageously configured to provide simultaneous stimulation and imaging within the limited dimensions, as described elsewhere herein.

As shown in FIG. 1 the microscope system 100 can include a plurality of components (e.g., optical elements) within the dimensions 120 and 122. Not shown is a further dimension, which extends perpendicular to the dimensions 120 and 122. Although not necessarily limited thereto, each of these dimensions can be less than an inch. In some cases, dimension 120 can be at most about 0.001 inch, 0.01 inch, 0.05 inch, 0.1 inch, 0.2 inch, 0.3 inch, 0.4 inch, 0.5 inch, 0.6 inch, 0.7 inch, 0.8 inch, 0.9 inch, 1 inch, or 5 inches. In some cases, dimension 122 can be at most about 0.001 inch, 0.01 inch, 0.05 inch, 0.1 inch, 0.2 inch, 0.3 inch, 0.4 inch, 0.5 inch, 0.6 inch, 0.7 inch, 0.8 inch, 0.9 inch, 1 inch, or 5 inches. In some cases the dimension extending perpendicular to the dimensions 120 and 122 can be at most about 0.001 inch, 0.01 inch, 0.05 inch, 0.1 inch, 0.2 inch, 0.3 inch, 0.4 inch, 0.5 inch, 0.6 inch, 0.7 inch, 0.8 inch, 0.9 inch, 1 inch, or 5 inches.

The microscope can be configured to magnify one or more portions of a sample such that a user can study the one or more portions of the sample that are outside a size range detectable by a user's eyes. The microscope system can be configured to magnify a portion of the sample that contains one or more objects of interest that a user can stimulate using the stimulation light. In some cases the microscope can be a relatively small microscope. The microscope may be mounted onto or attached to a living organism or a non-living organism. In some instances, the microscope may be mounted to an exterior of an organism (e.g., over skin of the organism). The microscope may be used to image a sample on or within the organism. For example, the microscope may be mounted to a head of a subject and used to image brain tissue of the organism. The microscope may be mounted to a subject and used to image any other tissue on or within the subject. Examples of samples may include any biological sample or tissue, such as nervous tissue (e.g., brain tissue), muscle tissue, connective tissue, cancerous tissue, organ tissue, cardiac tissue, vascular tissue, or epithelial tissue. A subject may be a human subject or an animal subject. In some embodiments, animal subjects may include rodents (e.g., mice, rats, rabbits, guinea pigs, gerbils, hamsters), simians (e.g., monkeys, chimpanzees, orangutans, gorillas, and humans), equines (e.g. horses), bovines (e.g., cows), canines (e.g., domestic dogs), felines (e.g., domestic cats), avines, insects, or any other types of animals. In some instances, the subjects may weigh less than about 50 kg, 40 kg, 30 kg, 20 kg, 15 kg, 10 kg, 5 kg, 3 kg, 2 kg, 1 kg, 750 grams, 500 grams, 400 grams, 300 grams, 200 grams, 100 grams, 75 grams, 50 grams, 40 grams, 30 grams, 25 grams, 20 grams, 15 grams, 10 grams, 5 grams, 3 grams, or 1 gram. In some embodiments, the microscope can be mounted on or inserted into a living organism or a non-living organism, and used for pre-clinical or clinical research. In some embodiments, the microscope can be used for clinical diagnostics, e.g., to determine a clinical diagnostic test result, or for therapeutic applications, e.g., for photostimulation of neuronal tissue. In some embodiments, the disclosed microscope or related optical systems may be used for imaging and/or photostimulation of neuronal tissue of the central nervous system. In some embodiments, the disclosed microscope or related optical systems may be used for imaging and/or photostimulation of neuronal tissue of the peripheral nervous system. In some embodiments, the disclosed microscope or related optical systems may be used for imaging and/or photostimulation of neuronal tissue of both the central and peripheral nervous systems.

The microscope (or an optical assembly thereof) can be coupled, optically and/or mechanically, to a probe inserted into an organism. The probe may or may not contact a tissue of the organism. The probe may be partially implanted in the tissue of the organism. The probe can deliver imaging light and stimulation light to a sample simultaneously. The probe can deliver imaging light and stimulation light to a sample directly. The probe can deliver imaging light and stimulation light to a sample without transmitting the imaging light and/or the stimulation light through a biological barrier such as skin or bone. The probe can comprise an objective lens. Alternatively, the probe may not include an objective lens.

The microscope can be used in vivo, or in vitro. In some instances, the microscope may be used in vivo for a subject that is conscious. The microscope may be used in vivo for a subject that is not anesthetized. The microscope may be used in vivo for a subject that may be freely moving or mobile. The subject may be able to freely walk around an environment while the microscope is connected to (e.g., mounted on, inserted within) the subject. The subject may be able to freely walk around an environment while the microscope is imaging a sample of the subject. A small microscope, such as those having dimensions as described elsewhere herein, may be advantageous to provide little interference with activities of the subjects, or to be used with smaller subjects, such as those having characteristics described herein.

At least a fraction of the optical elements (e.g., condenser lens, dichroic mirror, and filter elements) that direct the imaging and/or stimulation light to the sample can be outside of an optical path that directs light emission from the sample to the image sensor. Placing at least a fraction of the optical elements that direct the imaging and/or stimulation light to the sample outside of the optical path between the sample and the image sensor can increase the efficiency of light transfer from the sample to the image sensor. Providing a high efficiency transfer of light from the sample to the image sensor can permit relatively low power density levels of imaging light to be delivered to the sample.

The microscope system described herein can simultaneously image and stimulate at least a portion of a sample without cross talk between the imaging light and the stimulation light. Cross talk can occur when the imaging light accidentally stimulates at least a portion of the sample such that the stimulation is not entirely controlled by the stimulation light only. Similarly cross talk can occur when the stimulation light reflects off the sample and/or causes fluorescence of the sample and causes stray light to be delivered to the image sensor.

The number of photons delivered to the sample per unit area required to generate an image of the sample can be minimized or reduced by optimizing the efficiency of the light collection path between the sample and the image sensor. Reducing the power density of the imaging light directed to the sample can decrease the probability of accidentally stimulating the target object with the imaging light. The low level of imaging light relative to the stimulation light can minimize cross talk between the imaging and stimulation light. Cross talk can occur when imaging light inadvertently stimulates one or more portions of the sample. The portion of the sample (e.g., opsin) that is stimulated by the stimulation light can be similarly stimulated by the imaging light if the power density of the imaging light exceeds a predetermined threshold. This predetermined threshold hold can be decided by a variety of factors including the type of opsin, the concentration of the opsin in the cell membrane, and the wavelength of the imaging light. A user may want to reduce the probability of unintentionally stimulating one or more portions of the sample by the imaging light while intentionally providing stimulation light to one or more portions of the sample. The systems and methods described herein provide an efficient optical path with few optical elements between the sample and the image sensor that permits use of low levels (e.g., power density) of imaging light. The level of imaging light used in the system described herein can be below a level that stimulates one or more portions of the sample.

In some cases the stimulation light source and the imaging light can be provided at substantially the same power. Cross talk between the stimulation light source and the imaging light source at substantially the same power can be reduced by spectral separation of the stimulation light source and the imaging light source. Alternatively or additionally, cross talk between the imaging light source and the stimulation light source can be reduced with a filter array. Alternatively or additionally, cross talk between the imaging light source and the stimulation light source can be reduced with baffles configured to physically separate the light from the light sources.

Emission from the sample can be collected by one or more light detectors (e.g., pixels) of the image sensor to generate an electronic representation of an image of the sample. In some cases, the emission can be a fluorescence emission stimulated by the imaging light. Stimulation light can reflect off of the sample and/or induce fluorescence emission which can cause cross talk between the imaging light and the stimulation light during imaging. Cross talk from reflection and/or fluorescence from the stimulation light can be reduced or eliminated by providing spectral separation between the imaging light and the stimulation light. In some cases, the imaging light and stimulation light incident on the sample can be spectrally separated by providing the imaging light at a first wavelength and the stimulation light at second wavelength that is substantially higher or lower than the first wavelength. In some cases, the discrete wavelength or range of wavelengths of the imaging light and the discrete wavelength or range of wavelengths of the stimulation light can be spectrally separated by at least about 5 nm, 10 nm, 20 nm, 30 nm, 40 nm, 50 nm, 60 nm, 70 nm, 80 nm, 90 nm, 100 nm, 200 nm, 300 nm, 400 nm, 500 nm, 600 nm, 700 nm, 800 nm, 900 nm, 1000 nm. In some cases, the spectral separation between the imaging light and the stimulation light can be less than 5 nm. The spectral separation between the imaging light and the stimulation light can fall between any of the values listed herein.

A wavelength of an emission (e.g., fluorescence) emitted by the sample in response to the imaging light can be a function of a known wavelength of the incident imaging light such that a filter can be used to separate light that is not within the expected wavelength range before the light is detected by the image sensor. In some cases, the light that is outside of the expected range can be unwanted emission from the sample caused by the stimulation light. Different filters can be used for different samples or different types of imaging studies such that the discrete wavelength or range of wavelengths of the imaging and/or stimulation light can be varied. In some cases, the imaging light (e.g., fluorescence excitation light) can be provided at a wavelength of about 100 nm, 200 nm, 300 nm, 400 nm, 500 nm, 600 nm, 700 nm, 800 nm, 900 nm, 1000 nm, 1100 nm, 1200 nm, 1300 nm, 1400 nm, 1500 nm, 1600 nm, 1700 nm, 1800 nm, 1900 nm, or 2000 nm. The imaging light can be provided at a wavelength greater than the values listed, less than the values listed, or at a value between any of the values listed. In some cases, the stimulation light (e.g., optogenetic stimulation light) can be provided at a wavelength of about 100 nm, 200 nm, 300 nm, 400 nm, 500 nm, 600 nm, 700 nm, 800 nm, 900 nm, 1000 nm, 1100 nm, 1200 nm, 1300 nm, 1400 nm, 1500 nm, 1600 nm, 1700 nm, 1800 nm, 1900 nm, or 2000 nm. The stimulation light can be provided at a wavelength greater than the values listed, less than the values listed, or at a value between any of the values listed. The imaging light can be provided over a range of wavelengths. The stimulation light can be provided over a range of wavelengths. The range of wavelengths of the imaging light can be larger compared to the range of wavelengths of the stimulation light. Alternatively, the range of wavelengths of the imaging light can be smaller compared to the range of wavelengths of the stimulation light. In some cases, the range of wavelengths of the imaging light and the range of wavelengths of the stimulation light can have at least a fraction of overlapping range. FIG. 6 shows a graphical example of a spectrally separated imaging light and stimulation light. The graphs 600 and 606 each show intensity as a function of wavelength. In graph 600, the imaging light 601 emits light at a shorter wavelength range than the stimulation light 602. For example, the imaging light can emit in a first range of wavelengths 603. The stimulation light can emit in a second range of wavelengths 604. A gap 605 can be provided between the first range of wavelengths 603 and the second range of wavelengths 604. In graph 606, the imaging light 607 emits light at a longer wavelength than the stimulation light 608. For example, the imaging light can emit in a first range of wavelengths 610. The stimulation light can emit in a second range of wavelengths 611. A gap 609 can be provided between the first range of wavelengths 610 and the second range of wavelengths 611.

In some cases, the power density of the imaging light required for imaging can be further reduced by providing close proximity between an optical source of imaging (e.g., excitation) light and the sample. For epi-fluorescent imaging, the interaction between the imaging light and the sample causes the generation of fluorescence emission from the sample. The imaging light can be directed toward the target object and may have a specific wavelength configured for absorption by fluorophores, fluorescent markers or fluorescent probes. The fluorophores then emit light at different (e.g., longer) wavelengths. Different fluorophores can emit light at different wavelengths (e.g., colors). The amount of absorbed light can be related to the power density of the imaging light delivered to the target object. In this manner, the amount of fluorescence generated is correlated to the power density of the imaging light. Although various light delivery mechanisms can help reduce the attenuation of light as it travels through a medium, the attenuation of light will increase as distance of travel through a medium increases. Also, when using air and other mediums, the composition of the medium and other dispersive attributes can play significant roles in the delivery and/or attenuation of the light. In some instances, the microscope system can be designed to permit the imaging light to be arranged in close proximity to the sample, thereby facilitating the use of a relatively low power imaging light source. In some cases, a linear distance between the optical source of the imaging light and the target object (e.g., the tissue-to-imaging light source path length) can be at most about 5 cm, 2 cm, 1 cm, 5 mm, 1 mm, 0.1 mm, 0.01 mm, 0.001 mm, 0.0005 mm, or 0.0001 mm.

Similarly, image resolution can be dependent on the amount of light transmitted from the sample to the image sensor. In some cases, a linear distance between the sample and the image sensor (e.g. the tissue-to-image sensor path length) can be at most about 5 cm, 2 cm, 1 cm, 5 mm, 1 mm, 0.1 mm, 0.01 mm, 0.001 mm, 0.0005 mm, or 0.0001 mm. A linear distance between an objective lens that focuses light emitted from the sample and the image sensor can be at most about 5 cm, 2 cm, 1 cm, 5 mm, 1 mm, 0.1 mm, 0.01 mm, 0.001 mm, 0.0005 mm, or 0.0001 mm. A linear distance between an objective lens focal plane and the image sensor can be at most about 5 cm, 2 cm, 1 cm, 5 mm, 1 mm, 0.1 mm, 0.01 mm, 0.001 mm, 0.0005 mm, or 0.0001 mm.

Various fluorescence sources can be used consistent with one or more embodiments discussed herein. The mention of a particular source of fluorescence does not necessarily preclude use of other sources of fluorescence (e.g., genetically-encoded fluorescent proteins, such as GFP, GCaMP, mCherry, and variants thereof).

Embodiments of the present disclosure relate to a microscope device and system that captures image data for a relatively large field-of-view, the image data providing high resolution of a sample. The field-of-view can be at least about 0.1 mm$^2$, 0.2 mm$^2$, 0.3 mm$^2$, 0.4 mm$^2$, 0.5 mm$^2$, 1 mm$^2$, or 5 mm$^2$. The entire field-of-view can be imaged at once. Stimulation light can be directed to any portion of the field-of-view or the entire field-of-view. The entire field-of-view can be imaged at once without dividing the field-of-view into subsets and scanning each subset individually to image the entire field-of-view. The entire field-of-view can be simultaneously captured at a high resolution. The entire field-of-view can be simultaneously captured with a resolution of at least about 0.1 µm, 0.5 µm, 1 µm, 2 µm, 3 µm, 4 µm, 5 µm, 10 µm, 20 µm, 30 µm, 40 µm, or 50 µm. The resolution can be sufficient to identify one or more cells in an image captured in the microscope system. The resolution can be sufficient to identify one or more cellular structures in an image captured by the microscope system. The resolution can be sufficient to identify one or more dendrites in an image captured by the microscope system. The resolution can be sufficient to identify one or more nerve cell axons in an image captured by the microscope system. The relatively large field-of-view can permit a user to stimulate two or more cells or cell populations in the same field-of-view to observe an interaction of the stimulated cells or cell populations.

The entire field-of-view can be imaged by processing of light from the sample directed to the image sensor. The image sensor can comprise an array of sensor elements or pixels, which is provided to image the field-of-view. The sensor elements detect light emission from the sample for different portions of the field-of-view. The sensor elements can be monochrome light detectors. The sensor elements can detect light in one or more predetermined wavelength ranges. The sensor elements can be configured with sufficient sensitivity and proximity to the sample to facilitate image capture and generation of at least a portion of the sample.

In some cases, operation of the microscope system described herein can generate heat within the microscope system. Internal resistance from one or more electronic circuit elements and/or one or more light sources can generate heat causing a surface temperature of the one or more optical elements, the microscope housing, or other components in thermal communication with the microscope system to increase. In some cases, the microscope system can be on or near a living tissue. This generated heat can place limits on a duration of time that the microscope can be used. The generated heat can be transferred to the living tissue can cause the living tissue to heat up. The living tissue can be heated to a temperature above which tissue dies, burns, decomposes, oxidizes, or otherwise degrades. In some cases, the generated heat can influence cellular activity and lead to observations that can confuse the results of an optogenetic experiment. Some cells may be more active at elevated temperatures such that the elevated temperatures result in observed cellular activity caused by the generated heat instead of the stimulation light. In some cases, one or more cooling fins, heat sinks or heat pipes can be placed on the microscope to remove the generated heat by radiation, conduction and/or convection. The cooling fins, heat pipes, or heat sinks can prevent and/or reduce heat transfer from the microscope system to the living tissue.

In some cases, the microscope can operate with relatively low optical magnification with high-resolution imaging of a field-of-view for one or more samples of small size. The magnification can be at most about 1000×, 500×, 100×, or 50×, 10×, 8×, 5×, 4×, 3×, 2×, 1.5×, or 1×. The low level of magnification may enable the microscope to attain a high level of resolution for the field-of-view as described elsewhere herein. A high level of resolution can be attained by the microscope system using a relatively low magnification. The maximum magnification capability of the optical magnification required for a particular level of imaging can be lessened through the careful design and application of a microscope device and system consistent with various aspects discussed herein.

The microscope system described herein permits real-time simultaneous imaging and stimulation of one or more portions of a sample using a microscope device and/or system consistent with aspects discussed herein. The microscope system can facilitate in vivo or in vitro real-time simultaneous imaging and stimulation of target objects. For instance, in vivo imaging and stimulation of a live subject can be particularly useful for correlating external stimuli and other factors with the captured images. This correlation can be used, for example, as a diagnostic/research tool by associating properties of the captured images with the external stimuli. Real-time imaging at high frame rates can further provide such correlation as a function of time.

The microscope system can permit a user to direct imaging light to a sample to image the sample and detect one or more portions of a sample that the user would like to stimulate. The user can then provide stimulation light to the one or more portions of the sample detected with the imaging light. The user can continue to observe the sample while the stimulation light is delivered to the one or more portions of the sample in real time. In an example, the user can observe a neural circuit in the sample with the microscope system. The user can direct stimulation light to a portion of the neural circuit and observe a response of one or more other portions of the neural circuit in real time. In some cases, the user can provide stimulation light to inhibit activity in one or more portions of the sample. The user can observe activity using the imaging light from the microscope system. When the user observes the activity the user can provide stimulation light to at least a portion of the sample to inhibit the activity. In an example, the user can observe activity between two or more neuron populations that is indicative of pre/early seizure activity. The user can provide stimulation light to the one or more neuron populations to prevent or ease the seizure.

The microscope device and/or system can have a modular design that facilitates detaching and reattaching various components of the microscope device. The detachment and reattachment can be used to replace the modular components with new and/or different modular components. For instance, a light source can be replaced with a new light source having the same or different optical and/or electrical properties. Either or both of the stimulation light source and the imaging light source can be replaceable. The array of optical sensors and/or the optical direction elements (e.g., mirrors, filters and lenses) can also be removed and replaced. If desired, the optical sensor can also be removed and replaced.

The microscope system can include a synchronization circuit for interfacing to an external optical-data processing (recording and/or configuring) system. The synchronization circuit includes logic circuitry (e.g., a programmable or semi-programmable chip (microcontroller or ASIC) that is configured and arranged to communicate a frame reference/active signal. The synchronization circuit can include a field programmable gate array (FPGA). The synchronization circuit can include an ARM based microcontroller. In a typical application, a frame active signal would provide synchronization information, e.g., as defined in an IEEE communications standard, for and with the data communicated between the microscope system and the external system. Such an optical-data recording/configuring system can be used to install software, configure set-up parameters for experiments and procedures, provide visual feedback during such experiments and procedures, and record the optical data for manipulation and further study. The external optical-data processing (recording and/or configuring) system can be configured to control the stimulation light source as described elsewhere herein.

In yet further embodiments the instant disclosure is directed to methods of using the image devices which are described herein. Certain of the disclosed devices and systems may include a baseplate acting as a foundational structure which provides support/stability and also allows for microscope or optical probe (re)alignment. These methods include the steps of attaching and reattaching the microscope or optical probes to the baseplate for allowing the microscope or optical probe alignment to be precise. Such precision should be sufficient for repeated imaging of a common imaging location, e.g., during chronic experiments. The baseplate can be attached to a living organism. The baseplate can attach to the head of a living organism. The baseplate can attach to the skull of the living organism. In some cases, the baseplate can remain attached to the living organism while the microscope is removed from the baseplate. The baseplate can be attached to the living organism with a helmet, belt, and/or harness.

In some cases, the microscope can be configured to simultaneously stimulate a portion of the sample and image (e.g., observe) a portion of the sample. The portion of the sample can comprise an object of interest. The object of interest can be an object that can be stimulated and/or deactivated by light energy. The object of interest can be one or more cells. The object of interest can be one or more nerve cells (e.g., neurons). A chosen one or more cells can be stimulated or deactivated by genetically loading light activated channels (e.g., opsins) into a cellular membrane of the chosen one or more cells. In some cases, the light activated channels can be activated by light of a specified wavelength and/or intensity. The wavelength of the stimulation light source can be modulated to activate different light activated channels.

Figure 2A:
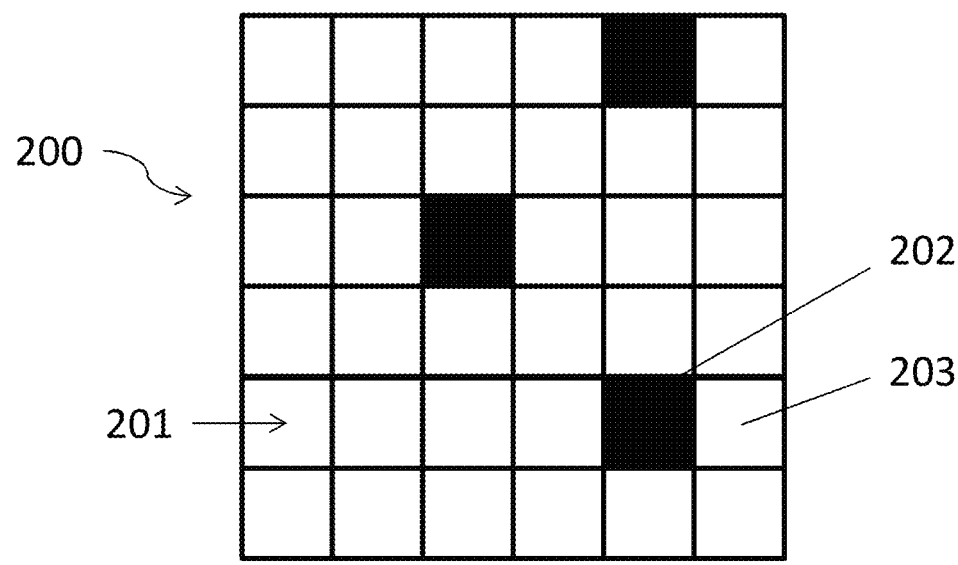
FIG. 2A shows a schematic of a stimulation light source comprising a plurality of light sources.

The stimulation light source can be a single light source. Alternatively, the stimulation light source 200 can comprise an array of light sources 201 as shown in FIG. 2A. The stimulation light source 200 can have an area of at least about 1 square micron, 5 square microns, 10 square microns, 50 square microns, 100 square microns, 0.001 square mm, 0.01 square mm, 0.1 square mm, 1 square mm, 5 square mm, 10 square mm, or 50 square mm. The stimulation light source 200 can comprise an array of 1×n light sources 201 where n can be an integer from 1 to 1000. In some cases the stimulation light source can comprise a matrix of m×n light sources where m can be an integer from 1 to 1000 and n can be an integer from 1 to 1000. In some cases, a matrix of light sources can permit stimulation of an individual cell, portion of a sample, or object. The matrix of light sources can permit stimulation of an individual neuron or an individual population of neurons. The light sources can be light emitting diodes (LEDs). The light sources can be organic light emitting diodes (OLEDs). The light sources can be micro-LEDs. The light sources can be high-power LEDs. The light sources can be directed through a spatial light modulator. The light sources can include light patterned through a coupled fiber bundle. The light sources can include a pattern of laser diodes. In some cases, the high-power LEDs can emit light with a power of at least about 0.1 W, 0.25 W, 0.5 W, 0.75 W, 1 W, 2 W, 3 W, 4 W, 5 W, 10 W, 15 W, 20 W, or 25 W.

The stimulation light source can be in communication with a controller. The stimulation light source can be in communication with a controller through a wired or wireless connection. The controller can be on-board or off board the microscope. The controller can comprise one or more processors programmed to control the stimulation light source. One or more of the stimulation light sources in the matrix or array can be turned on by the controller to provide stimulation light to a specified location on the target object in order to deliver stimulation light to an object of interest (e.g., cell). FIG. 2A shows a stimulation light source 200 with a plurality of turned on light sources 202 and a plurality of turned off light sources 203. Any number of light sources can be turned on in the stimulation light source. For example, zero, one, two, three, four, five, or more light sources can be turned on in the stimulation light source 200. Any number of light sources can be turned off in the stimulation light source. For example, zero, one, two, three, four, five or more light sources can be turned off in the stimulation light source 200. The stimulation light sources can be turned on in a pattern in order to deliver stimulation light to a specified region of the target object, for example to the one or more objects of interest. The one or more processors can be programmed to determine the pattern in which the one or more light sources should be turned on and off in order to deliver stimulation light to a specified region of the target object. The one or more processors can receive an image of the target object from the microscope as an input when determining the pattern. In an example a sample can comprise a plurality of nerve cells. A user can stimulate a single nerve cell in the sample without stimulating adjacent nerve cells by delivering stimulation light only to a fraction of the sample. A user can observe a reaction of the other unstimulated nerve cells to the one stimulated nerve cell.

Figure 2B:
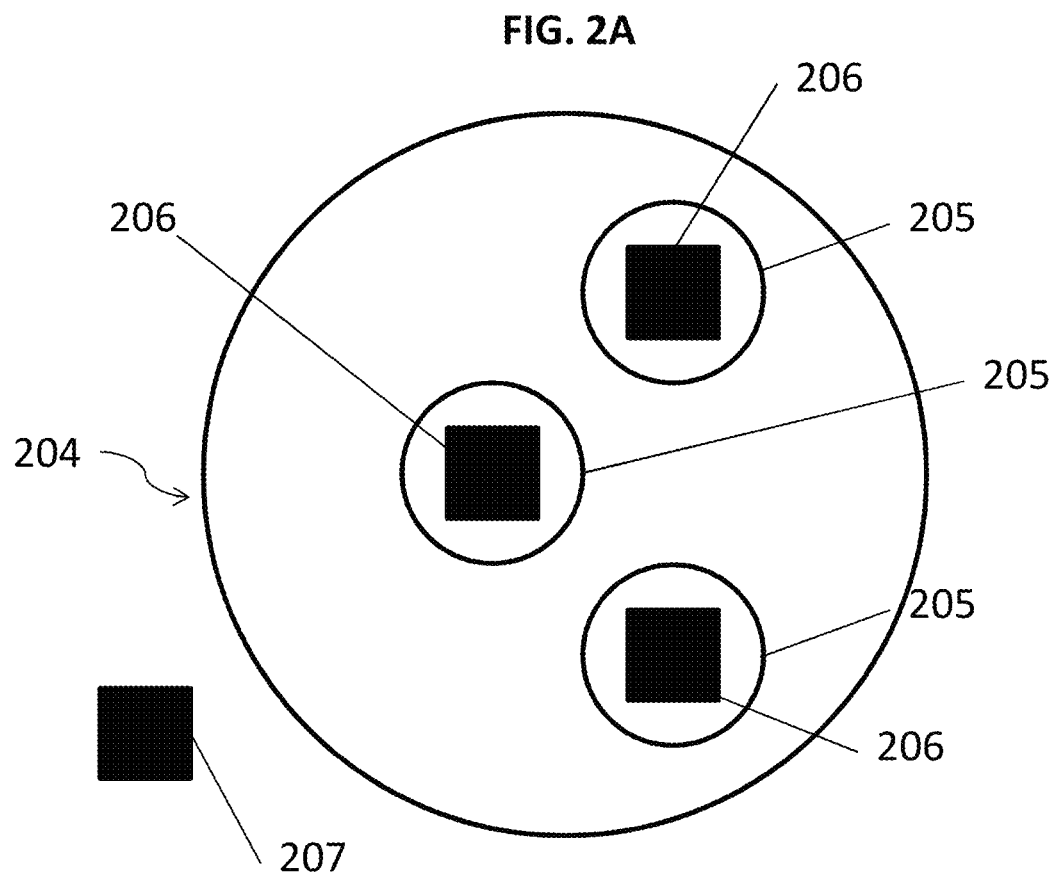
FIG. 2B shows a schematic of a field-of-view imaged by the microscope system, said field-of-view comprising a plurality of objects of interest upon which stimulation light is incident.

FIG. 2B shows a field-of-view 204 comprising the sample that can be imaged by the microscope system. The field-of-view 204 can comprise one or more objects of interest 205. The objects of interest 205 can be objects that respond to the stimulation light source. The objects of interest can be cells. The object of interest can be nerve cells. Stimulation light 206 can be incident on the objects of interest 205. The stimulation light can be incident on two or more objects of interest 205 simultaneously. The stimulation light can be incident on at least a fraction of the field-of-view 204. The stimulation light can be incident on at least about 1%, 5%, 10%, 20%, 30%, 40%, 50%, 60%, or 70% of a sample or a portion of a sample contained in the field-of-view 204. Imaging light can be provided to the field-of-view 204 while the stimulation light is provided to the one or more objects of interest 205 such that the reaction of the one or more objects of interest 205 to the stimulation light can be imaged. While the stimulation light 206 is shown to be smaller than the objects (e.g., cells) 205 that are being stimulated in FIG. 2B, it is to be understand that the stimulation light can be either smaller or larger than the objects of interest.

Alternatively or in addition, the stimulation light 207 may be incident on portions of the sample outside of the field-of-view. For example, the stimulation light may be incident on a different portion of the sample than the imaging light. For example, the field-of-view (e.g., imaging field-of-view) may be displayed (e.g., on a display) for observation by a viewer while stimulation light is incident on a different portion of the sample that is not displayed. In some instances, the stimulation light may stimulate a right side of the brain (e.g., mouse brain) while a field-of-view 204 comprising the objects of interest shows a left side of the brain, or vice versa. In some instances, the stimulation light may either fully or partially overlap with the imaging light (e.g., at the sample). In some instances, the stimulation light may not overlap with the imaging light. For example, the stimulation light may stimulate a right side of the brain (e.g., mouse brain) while an imaging light is incident on a left side of the brain, or vice versa. In some instances, the imaging light and the stimulation light may share at least a part of the same optical path. In some instances, the optical paths of the stimulation light and the imaging light may be independent. In some instances, the optical paths of the stimulation light and the imaging light may be different. The stimulation light and the imaging light may be temporally modulated as previously described herein. For example, the stimulating light may stimulate a portion of the sample while a portion (e.g., a different portion) of the sample is being illuminated by the imaging light.

The stimulation light sources can be turned on in a pattern configured to deliver stimulation light to one or more objects of interest shown in an image generated by the microscope system. The pattern can be a predetermined pattern. In some cases, the pattern can be chosen by a user and provided as an input to a computer system configured to control the stimulation light source. The computer system may generate a pattern. The computer system or a user may analyze an image of the field-of-view and generate a pattern or modification to an existing pattern in response to the analysis. The pattern may change over time or in response to the imaged sample. Feedback may be provided via an image of a response to an earlier stimulation pattern, which may be used to formulate a subsequent stimulation pattern. The computer system will be described in detail herein. The pattern can be a constant pattern. Alternatively the pattern can change over time. The pattern can change with a predetermined frequency. The pattern can change when the field-of-view changes to a different sample or a different region of a current sample.

The stimulation light can be provided to at least a portion of the sample containing one or more objects of interest with a predetermined pattern. The pattern can comprise illuminating one or more of the light sources in the matrix or array in a temporal sequence. The pattern can comprise illuminating one or more of the light sources in the matrix or array with a specific frequency, intensity, power, time duration, and/or wavelength distribution (e.g., discrete wavelength or range of wavelengths).

The stimulation light source and/or illumination light source can be controlled by a computer system. The simulation light source and/or illumination light source can be in communication with the computer system through a wireless or wired connection. The computer system can comprise one or more processors configured to execute a program that generates patterned stimulation of the target object by the stimulation light source. The program can generate the patterned stimulation using an algorithm. The algorithm can take one or more optical properties of the system as inputs when building the stimulation pattern. The optical property inputs can comprise optical components in the microscope, focal length of one or more light sources through the optical components, and/or light transmission of the one or more optical components (e.g., transmission, reflectance, and/or absorbance as a function of wavelength, frequency, and/or intensity). The algorithm can use an image generated by detection of imaging light as an input to identify one or more locations of target object in the field-of-view for stimulation by the stimulation light. The algorithm can perform image analysis to detect one or more objects of interest for delivery of stimulation light. The algorithm can determine which stimulation light sources in an array and/or matrix of stimulation light sources should be illuminated in order to direct stimulation light to the one or more objects of interest detected in the image. The algorithm can determine the power density of stimulation light needed to stimulate the one or more objects of interest detected in the image.

Figure 3:
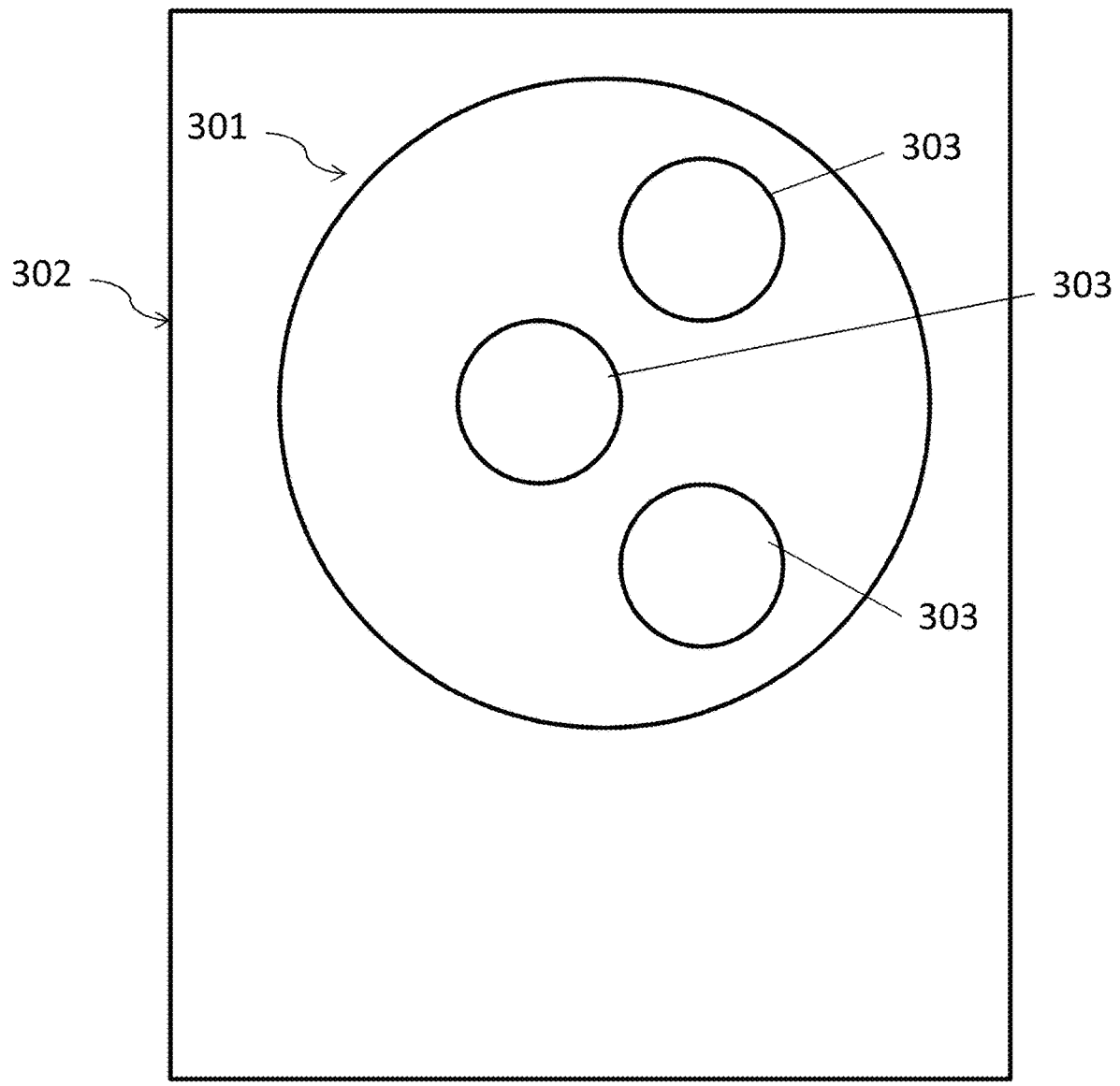
FIG. 3 shows a display that can be provided to a user to show a field-of-view imaged by the microscope system.

Alternatively or in addition to the algorithm a user can directly instruct the computer system to control the stimulation light source. A user can be an operator of the microscope system. The user can view an image of the field-of-view generated by the microscope system on a display device. FIG. 3 shows a schematic example of a field-of-view 301 that can be provided to the user on a display device 302. The field-of-view 301 can comprise one or more objects of interest 303. The user can select a specific stimulation pattern to be followed by the stimulation light source based on the location of the objects of interest shown on the display device 302. In some cases, a user can alter the stimulation light source pattern based on a response of the one or more objects of interest to the stimulation light. Alternatively or additionally, the one or more processors of the computer system can execute image analysis of the field-of-view to automatically detect the one or more objects of interest 303 and suggest or initiate a pattern to be followed by the stimulation light source to deliver stimulation light to the one or more objects of interest 303.

The user can specify a new stimulation pattern or the user can choose a previously used or generic stimulation pattern stored in a memory storage device on the computer system. A user can specify that the stimulation pattern change with time. The user can specify the frequency at which the stimulation pattern changes in time. A user can specify that the stimulation pattern change with each image captured by the microscope. The user can change the stimulation pattern while imaging the sample. In some cases, the user can change the stimulation pattern to target a specific object in or region of the sample based on one or more characteristics detected in an image of the sample in real time. For example a user can detect a population of neurons in the image of the sample and choose a stimulation light pattern to provide stimulation light to the population of neurons.

Figure 4:
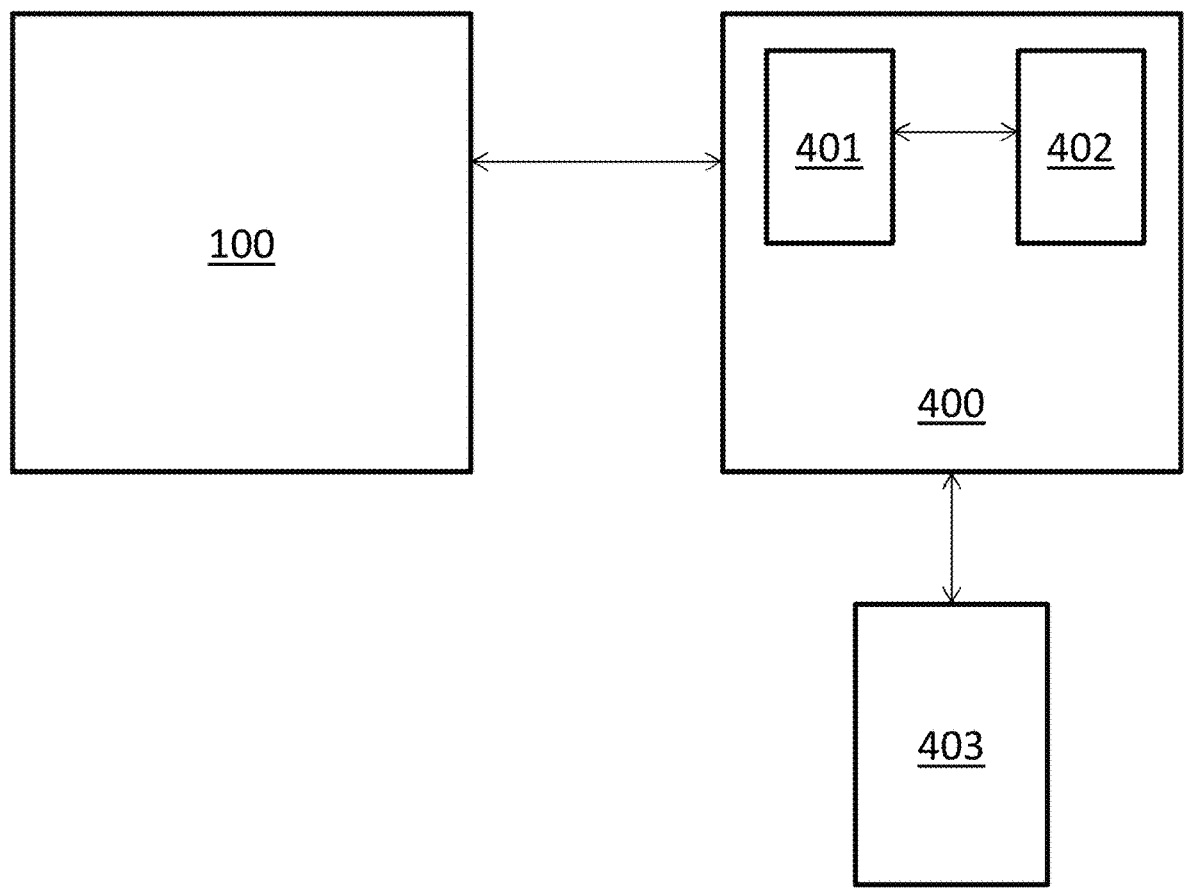
FIG. 4 shows a schematic of a small optogenetic microscope system in communication with a computer control system.

FIG. 4 shows a microscope system 100 in communication with a computer system 400. The microscope system 100 can be in communication with the computer system 400 through a wired or wireless connection. The computer system can comprise one or more processors 401. The one or more processors can be configured to execute one or more programs to control the microscope system. The processors can execute one or more programs to control the stimulation light source and/or the imaging light source of the microscope system. Instructions for the one or more programs can be stored on one or more memory storage devices 402. The one or more storage devices can be in communication with the one or more processors. At least a fraction of the memory storage devices can be part of a server in communication with the computer system.

A user can interact with the computer system through a user interface. The user interface can be provided in a display on a display device 403. The display device can be a monitor, screen, and/or electronic device in communication with the computer system 400. The display device 403 can be in communication with the computer system 400 though a wireless or wired connection. The user interface can be provided on a screen of a display device. The screen can be a liquid crystal display (LCD) screen or a touch screen. The display device can comprise a computer monitor. The display device can comprise and electronic device. The display device can be a hand held electronic device for example, a smartphone or tablet.

The microscope system can be configured to perform real-time simultaneous imaging and stimulation of target objects. The target object can be a living organism. The target objects can be conscious while the microscope system is operated. The microscope may be mounted onto a living organism or a non-living organism. In some instances, the microscope may be mounted to an exterior of an organism (e.g., over skin of the organism). The microscope may be used to image a sample on or within the organism. For example, the microscope may be mounted to a head of a subject and used to image brain tissue of the organism. The microscope may be mounted to a subject and used to image any other tissue on or within the subject.

The optogenetic microscope configured to simultaneously provide imaging and stimulation light described in detail herein can be used for various applications. For example the optogenetic microscope can be used to map regions of the brain of an organism. Connections between different nerve cells can be identified with the optogenetic microscope. The organism can be a living organism. In another example, the optogenetic microscope can be used to perform atrial fibrillation. The optogenetic microscope can be used to stimulate cardiac tissue in a living organism.

In another example, the optogenetic microscope can be used to stimulate light sensitive proteins. The light sensitive proteins can open or close ion channels or actively pump ions when stimulated by light from the optogenetic microscope.

Compact Optogenetic Microscope Systems Comprising an Adjustable Lens

Figure 7:
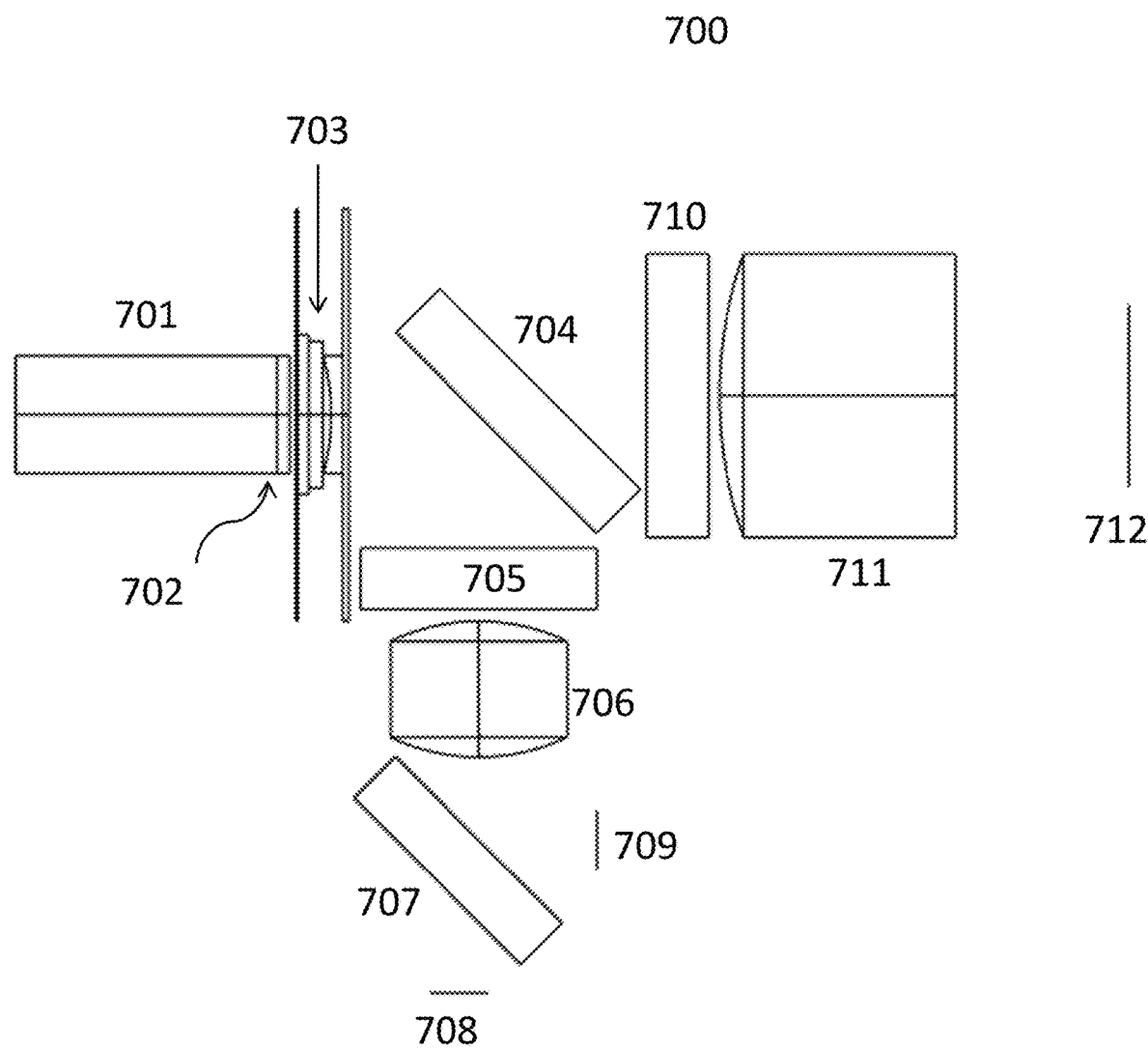
FIG. 7 shows a schematic of one embodiment of a compact optogenetic microscope system.

FIG. 7 illustrates one embodiment of a compact optogenetic microscope system 700 that comprises an adjustable lens 703 for adjusting the effective focal length and depth of field of the microscope system, or for correcting for chromatic aberration. Imaging light and stimulation light may be provided by light sources 708 and 709, and directed to the sample or subject by means of the optical path comprising dichroic mirror 707, lens 706, optical (excitation) filter 705, dichroic mirror 704, adjustable lens 703, optional corrective optical element 702, and/or gradient index (GRIN) lens 701. Imaging light reflected or scattered by the sample or subject is collected by GRIN lens 701, and transmitted to image sensor 712 by means of the optical path comprising optional corrective optical element 702, adjustable lens 703, dichroic reflector 704, optical (emission) filter 710, and lens 711. Similarly, fluorescence that is excited in the sample or subject by the stimulation light is collected by GRIN lens 701, and transmitted to image sensor 712 by means of the common optical path comprising optional corrective optical element 702, adjustable lens 703, dichroic reflector 704, optical (emission) filter 710, and lens 711. In combination with the transmittance properties of optical filters 705 and 710, the transmittance and reflectance properties of dichroic mirrors 707 and 704 determine the optical bandwidths of the imaging and stimulation light, as well as that for reflected or scattered imaging light and fluorescence light that reach the image sensor 712.

In some embodiments, GRIN lens 701 and optional corrective optical element 702 comprise the "objective" lens of the microscope system and are operably coupled to other lens elements. In some embodiments, GRIN lens 701 and optional corrective optical element 702 are components of an endoscopic probe attached to or optically coupled to other elements of the microscope system, wherein the endoscopic probe is designed to make contact with or be inserted into (e.g., partially implanted in) the sample or subject. Optionally, the corrective optical element 702 may be integrated with the GRIN lens 701. In some embodiments, the endoscopic probe may further comprise a cannula, e.g., a glass cannula, which is implanted in the sample or subject and into which the endoscopic probe is inserted. In some embodiments, the endoscopic probe may be a shared optical component of the illumination optical path, the stimulation optical path, and the imaging optical path, or any combination thereof. In some embodiments, more than one endoscopic probe may be utilized, wherein a different endoscopic probe is utilized by the illumination optical path, the stimulation optical path, the imaging optical path, or any combination thereof. In some embodiments, corrective optical element 702 compensates for the optical properties of GRIN lens 701 or an endoscopic probe comprising GRIN lens 701 to provide a toroidal object field having improved spatial resolution across the microscope's field-of-view. In those embodiments in which optional corrective optical element 702 is used, it is preferentially placed in contact with, or in close proximity to, the end of GRIN lens 701 that is distal from the sample or subject, although other placements are possible.

In some embodiments, the compact optogenetic microscope system may comprise additional apertures, lenses, optical filters, dichroic mirrors, prisms, mirrors, beam splitters, polarizers, etc., to further refine the optical properties (e.g., wavelength, polarization, or intensity) or physical dimensions of the imaging and stimulation light beams delivered to the sample or subject. Similarly, the compact optogenetic microscope system may comprise additional apertures, lenses, optical filters, dichroic mirrors, prisms, mirrors, beam splitters, polarizers, etc., to further refine the optical properties or physical dimensions of the imaging and fluorescence light beams delivered to the image sensor.

Each of the components depicted in FIG. 7 may be contained within a single housing as substantially described elsewhere, e.g., with respect to FIG. 1. In some embodiments, the components depicted in FIG. 7 may be configured in such a way that they are contained in two or more separate housings. Alternatively, some of the components depicted in FIG. 7 may be contained within a single housing, or two or more housing, while other elements are located outside of the single housing, or two or more housings. For example, GRIN lens 701 and optional corrective optical element 702 may be located outside a single housing while the other components are located within the single housing. GRIN lens 701 and/or optional optical corrective element 702 may or may not be in direct contact with other optical elements such as adjustable lens 703. As illustrated in FIG. 7, in some embodiments, GRIN lens 701 and/or optional corrective optical element 702 are placed in direct contact with, or in close proximity to, adjustable lens 703, e.g. in close proximity to the end of the GRIN lens 701 (or optional corrective optical element 702) that is farthest from the sample or subject (or tissue thereof). In some embodiments, the optical components comprising the imaging light delivery optical path and the stimulation light delivery optical path may be separated from those comprising the reflected or scattered imaging and fluorescence light collection optical path, and may be packaged in separate housings (e.g., as optical illumination, stimulation, and imaging probes). In some embodiments, the optical components comprising the imaging light delivery optical path and those comprising the light collection optical path may be packaged separately from the stimulation light delivery path (e.g., as an alternative form of an optical imaging probe). In some embodiments, the optogenetic microscope and optical probe housings may be configured to be removably attached to a common baseplate for mounting on a subject, such that two or more complete microscopes, optical illumination probes, optical stimulation probes, or optical imaging probes, or any combination thereof, may be removably attached to the common baseplate at fixed or adjustable relative positions, and wherein the optical axes for the two or more microscopes, optical illumination probes, optical stimulation probes, or optical imaging probes are substantially parallel to each other. In some embodiments, the common baseplate may be configured such that the optical axes for the two or more microscopes, optical illumination probes, optical stimulation probes, or optical imaging probes are not substantially parallel to each other. In some embodiments, at least 1, 2, 3, 4, 5, 6, 7, 8, or more microscopes or optical probes may be attached to the common baseplate. In some embodiments, the configuration of the common baseplate determines the lateral distance between one or more microscopes, optical imaging probes, and optical stimulation probes. In many embodiments, the baseplate is designed to be mounted on the subject in a fixed position, and therefore provide reproducible alignment to the attached optical assemblies (e.g. microscopes, optical illumination probes, optical stimulation probes, or optical imaging probes) relative to tissue of the subject. In embodiments where separate optical stimulation probes and optical imaging probes are attached to a common baseplate, the area of the sample or subject that is illuminated by the optical stimulation probe may overlap partially, completely, or not at all with the area of the sample or subject (e.g., the field-of-view (FOV)) from which reflected or scattered imaging light and fluorescence are collected and imaged onto the image sensor of the optical imaging probe or microscope.

As disclosed throughout this application, the imaging light source (FIG. 7, 708 or 709) may comprise one or more LEDs, or other types of light emitting elements. The imaging light source may provide essentially monochromatic light. Alternatively the imaging light source may provide imaging light at multiple wavelengths. In one non-limiting example, the imaging light source may comprise two or more LEDs or other light emitting elements that emit light of different colors (e.g., different wavelength ranges). The imaging light source may provide light for single-color or multi-color imaging. In some embodiments, the imaging light source may comprise two or more light-emitting elements, e.g., LEDs, that are configured to emit light in user-defined spatial patterns and/or in user-defined temporal patterns. In these embodiments, the user-defined spatial pattern may have a spatial resolution at the focal plane of at least may be at least 0.1 µm, at least 0.5 µm, at least 1 µm, at least 5 µm, or at least 10 µm, at least 15 µm, at least 20 µm. In some embodiments, the compact optogenetic microscope system further comprises a processor and a memory device, wherein the processor is configured to execute a series of software-encoded instructions stored in the memory device. In some embodiments, the software-encoded instructions include instructions for: (i) modulating the imaging light intensity in a time-dependent or spatially-dependent manner, (ii) modulating the stimulation light intensity in a time-dependent or spatially-dependent manner, (iii) varying the focal depth in a time-dependent manner, and (iv) capturing one or more images of the tissue within the specified field-of-view at specified times, or any combination thereof. In some embodiments, e.g., wherein the tissue is brain tissue, the software-encoded instructions may comprise instructions for modulating the stimulation light in a time-dependent or spatially-dependent manner to induce a neurological response in said brain tissue, e.g., a therapeutic effect.

In many embodiments, the imaging light source is integrated with the optical elements configured to deliver imaging and/or stimulation light to the sample and is packaged within the same housing. In some embodiments, the imaging light source may be located externally to the housing that encloses the optical elements that deliver imaging and/or stimulation light to the sample, and optically coupled to the latter by means of, e.g., an optical fiber, a liquid light guide, or any other suitable means of guiding light. The imaging light source is configured to deliver imaging light to a sample or subject, or to tissue within a specified field-of-view within the subject, by means of the optical elements comprising a light delivery optical path.

As disclosed throughout this application, the stimulation light source (FIG. 7, 709 or 708) may also comprise one or more LEDs, or other types of light emitting elements. The stimulation light source may provide essentially monochromatic light. Alternatively the stimulation light source may provide stimulation light at multiple wavelengths. In one non-limiting example, the stimulation light source may comprise two or more high-intensity LEDs or other light emitting elements that emit light of different colors (e.g., different wavelength ranges). The stimulation light source may provide light for single-color or multi-color stimulation (excitation). In some embodiments, the stimulation light source may comprise two or more light-emitting elements, e.g., high intensity LEDs, that are configured to emit light in user-defined spatial patterns and/or in user-defined temporal patterns. In many embodiments, the stimulation light source is integrated with the optical elements configured to deliver imaging and/or stimulation light to the sample and is packaged within the same housing. In some embodiments, the stimulation light source may be located externally to the housing that encloses the optical elements that deliver imaging and/or stimulation light to the sample, and optically coupled to the latter by means of, e.g., an optical fiber, a liquid light guide, or any other suitable means of guiding light. The stimulation light source is configured to deliver stimulation light to a sample or subject, or to tissue within a specified illumination area or field-of-view within the subject, by means of the optical elements comprising a light delivery optical path.

As disclosed throughout this application, the image sensor 712 may comprise a monochromatic image sensor or a color image sensor. In some embodiments, the compact optogenetic microscope system may comprise two or more image sensors. Examples of suitable image sensors include, but are not limited to, CCD sensor chips and CMOS image sensors. In some embodiments, the image sensor captures a single image or a series of images, which may be greyscale or RGB images. The single image or series of images may be captured before, during, or after delivery of stimulation light to the sample or subject using predefined or user-adjustable exposure times. In some embodiments, the timing of image capture by the image sensor may be synchronized with the timing for spatial and/or temporal modulation of the delivery of stimulation light to the subject or sample. In some embodiments, the timing of image capture by the image sensor maybe offset (out of phase) with the timing for spatial and/or temporal modulation of the delivery of stimulation light to the sample or subject. Light that is reflected, scattered, or emitted (e.g., upon excitation by stimulation light) by the sample or subject, or by tissue within a subject, is collected and delivered to the image sensor by means of the optical elements comprising a light collection optical path.

The adjustable lens 703 in FIG. 7 may comprise a deformable lens. Alternatively or in addition, the adjustable lens may comprise movable components, e.g. movable optical elements. The adjustable lens may be adjusted by electro-optical means, mechanical means, electro-mechanical means, thermo-optical means, and/or acousto-mechanical means. For example, by applying voltage to the lens and/or components associated with the adjustable lens, a focal length of the lens may be adjusted. For example, by applying voltage to the lens and/or components associated with the adjustable lens, the lens may be tilted. An adjustable lens adjustable by any electrically-related means may herein also be referred to as an electronic lens or "e-lens". In many embodiments, at least one adjustable or deformable lens may constitute an optical element that is shared by the optical paths by which imaging light and stimulation light are transmitted to the sample. In these embodiments, the at least one shared adjustable or deformable lens may be positioned in close proximity to the end of the GRIN lens (or optional corrective optical element) that is farthest from the sample or tissue. In some embodiments, the compact optogenetic microscope system may comprise two or more adjustable lenses configured, for example, to separately adjust the effective focal length of the stimulation and image collection light paths, thereby ensuring that stimulation light is focused on the same focal plane that is used as the field-of-view by the image collection optics. In some embodiments, the effective focal length of the stimulation and image collection light paths may be adjusted to ensure that stimulation light is focused on a different focal plane than that used as the field-of-view by the image collection optics. In some embodiments, the effective focal length is adjustable such that the focal plane for the stimulation light and/or that for the image collection optics is adjustable over a range of about 50 µm, about 100 µm, about 200 µm, about 300 µm, about 400 µm, or about 500 µm, without loss of spatial resolution.

In some instances, the adjustable lens may comprise a piezoelectric component or a mechanical component. For example, a lens fluid may be pumped into or out of a lens enclosure which expands or retracts the lens membrane to achieve varying focus and/or zoom. For example, an actuator may push or release a deformable wall to change a volume of liquid in a chamber to adjust a curvature of a lens, e.g. liquid lens. In some instances, voltage applied to a piezoelectric component may deform a thin membrane, e.g. a thin glass membrane that is in contact with a liquid or polymer layer coated on a substrate, thereby deforming the liquid or polymer layer and changing its optical properties. As non-limiting examples, the adjustable lens may comprise a liquid lens, a liquid-crystal lens, and/or a piezoelectric tunable lens, or any combination thereof.

The adjustable lens may comprise a size amenable for integration with the small microscope system described throughout. In some instances, the adjustable lens may comprise a radius equal to or less than about 1 mm, 2 mm, 3 mm, 4 mm, 5 mm, 6 mm, 7 mm, 8 mm, 9 mm, 10 mm, 12 mm, 14 mm, 16 mm, 18 mm, or 20 mm. Optionally, the adjustable lens may comprise variable radii. In some instances, the adjustable lens may comprise a thickness or height equal to or less than about 1 mm, 2 mm, 3 mm, 4 mm, 5 mm, 6 mm, 7 mm, 8 mm, 9 mm, 10 mm, 12 mm, 14 mm, 16 mm, 18 mm, or 20 mm. Optionally, the adjustable lens may comprise variable height.

The adjustable lens may comprise adjustable optical parameters. For example, the adjustable lens may comprise a variable focal length. As another example, the adjustable lens may comprise a variable optical axis. In some instances, the adjustable lens may be tilted and/or dithered. The adjustable lens may or may not be tilted about its optical axis. In some instances, an optical axis of the adjustable lens may be tilted or adjusted. The adjustable lens may be utilized, for example, for bringing images into focus, changing the effective focal depth to enable volumetric imaging, and/or for correcting chromatic aberrations.

In some embodiment, the adjustable lens may comprise a focal length equal to or more than about 10 mm, 15 mm, 20 mm, 25 mm, 30 mm, 40 mm, 50 mm, 60 mm, 70 mm, 80 mm, 90 mm, or 100 mm, or any focal length within this range. In some embodiments, the adjustable lens may be adjusted to have any of the previously referred to focal lengths at any given point in time.

In some embodiments, the adjustable lens may comprise a negative focal length or a focal length of infinity. In some embodiments, the adjustable lens may provide for a refractive power of about −100 to about +100 diopters, where diopter is defined as the reciprocal of the focal length in units of meters. In some embodiments, the adjustable lens may provide for refractive power of at least −100 diopters, at least −90 diopters, at least −80 diopters, at least −70 diopters, at least −60 diopters, at least −50 diopters, at least −40 diopters, at least −30 diopters, at least −20 diopters, at least −10 diopters, at least 0 diopters, at least +10 diopters, at least +20 diopters, at least +30 diopters, at least +40 diopters, at least +50 diopters, at least +60 diopters, at least +70 diopters, at least +80 diopters, at least +90 diopters, or at least +100 diopters. In some embodiments, the adjustable lens may provide for a refractive power of at most +100 diopters, at most +90 diopters, at most +80 diopters, at most +70 diopters, at most +60 diopters, at most +50 diopters, at most +40 diopters, at most +30 diopters, at most +20 diopters, at most +10 diopters, at most +0 diopters, at most −10 diopters, at most −20 diopters, at most −30 diopters, at most −40 diopters, at most −50 diopters, at most −60 diopters, at most −70 diopters, at most −80 diopters, at most −90 diopters, or at most −100 diopters. Any of the lower and upper values described in this paragraph may be combined to form a range included within the disclosure, such as the adjustable lens may provide a refractive power that ranges from about +20 diopters to about +70 diopters. Those of skill in the art will recognize that the adjustable lens may provide a refractive power having any value within this range, e.g., about +25 diopters.

Tilting an adjustable lens as referred herein may refer to tilting the adjustable lens itself. Alternatively or in addition, tilting the adjustable lens may refer to adjusting the adjustable lens (e.g. deforming the lens, adjusting a curvature of the liquid lens) such that an optical axis of the adjustable lens is tilted or varied. The tilt angle may or may not be about the optical axis of the adjustable lens. Optionally, the adjustable lens may be configured to be tilted an a tilt angle equal to or more than about 0.1°, 0.2°, 0.3°, 0.4°, 0.6°, 0.8°, 1°, 1.2°, 1.5°, 2°, 2.5°, 3°, 4°, or 5°.

In some embodiments, the disclosed optogenetic microscopes, or component optical probes, may comprise at least 1 adjustable or deformable lens, at least 2 adjustable or deformable lenses, at least 3 adjustable or deformable lenses, at least 4 adjustable or deformable lenses, or more. In those embodiments utilizing one or more adjustable or deformable lenses, the effective focal depth of the compact optogenetic microscope system or optical imaging probes may be varied to enable volumetric imaging, as referenced above. In such embodiments, the optogenetic microscope or optical imaging probes may be capable of collecting light and generating images over a sample or tissue volume of about 1 mm×1 mm×50 µm deep, or about 1 mm×1 mm×100 µm deep, or about 1 mm×1 mm×200 µm deep, or about 1 mm×1 mm×300 µm deep, or about 1 mm×1 mm×400 µm deep, or about 1 mm×1 mm×300 µm deep.

In some embodiments, the illumination area, stimulation area, and/or field-of-view (FOV) for the microscope system or optical probes may range from about 100 µm×100 µm to about 5 mm×5 mm. In some embodiments, the FOV is at least 100 µm×100 µm, at least 200 µm×200 µm, at least 300 µm×300 µm, at least 400 µm×400 µm, at least 500 µm×500 µm, at least 600 µm×600 µm, at least 700 µm×700 µm, at least 800 µm×800 µm, at least 900 µm×900 µm, at least 1 mm×1 mm, at least 1.1 mm×1.1 mm, at least 1.2 mm×1.2 mm, at least 1.3 mm×1.3 mm, at least 1.4 mm×1.4 mm, at least 1.5 mm×1.5 mm, at least 1.6 mm×1.6 mm, at least 1.7 mm×1.7 mm, at least 1.8 mm×1.8 mm, at least 1.9 mm×1.9 mm, at least 2 mm×2 mm, at least 2.5 mm×2.5 mm, at least 3 mm×3 mm, at least 3.5 mm×3.5 mm, at least 4 mm×4 mm, at least 4.5 mm×4.5 mm, or at least 5 mm×5 mm. In some embodiments, the FOV is at most 5 mm×5 mm, at most 4.5 mm×4.5 mm, at most 4 mm×4 mm, at most 3.5 mm×3.5 mm, at most 3 mm×3 mm, at most 2.5 mm×2.5 mm, at most 2 mm×2 mm, at most 1.9 mm×1.9 mm, at most 1.8 mm×1.8 mm, at most 1.7 mm×1.7 mm, at most 1.6 mm×1.6 mm, at most 1.5 mm×1.5 mm, at most 1.4 mm×1.4 mm, at most 1.3 mm×1.3 mm, at most 1.2 mm×1.2 mm, at most 1.1 mm×1.1 mm, at most 1 mm×1 mm, at most 900 µm×900 µm, at most 800 µm×800 µm, at most 700 µm×700 µm, at most 600 µm×600 µm, at most 500 µm×500 µm, at most 400 µm×400 µm, at most 300 µm×300 µm, at most 200 µm×200 µm, or at most 100 µm×100 µm. Any of the lower and upper values described in this paragraph may be combined to form a range included within the disclosure, such as the illumination/stimulation area and FOV may range from about 800 µm×800 µm to about 1.2 mm×1.2 mm. Those of skill in the art will recognize that the illumination/stimulation and FOV may have any value within this range, e.g., about 1.15 mm×1.15 mm.

In some embodiments, the effective focal depth of the microscope system may range from about 10 µm to about 1 mm. In some embodiments, the effective focal depth may be at least 10 µm, at least 25 µm, at least 50 µm, at least 75 µm, at least 100 µm, at least 200 µm, at least 300 µm, at least 400 µm, at least 500 µm, at least 600 µm, at least 700 µm, at least 800 µm, at least 900 µm, or at least 1 mm. In some embodiment, the effective focal depth may be at most 1 mm, at most 900 µm, at most 800 µm, at most 700 µm, at most 600 µm, at most 500 µm, at most 400 µm, at most 300 µm, at most 200 µm, at most 100 µm, at most 75 µm, at most 50 µm, at most 25 µm, or at most 10 µm. Any of the lower and upper values described in this paragraph may be combined to form a range included within the disclosure, such as the effective focal depth may range from about 200 μm to about 500 μm. Those of skill in the art will recognize that the effective focal depth may have any value within this range, e.g., about 275 μm. In some embodiments, the effective focal depth of the microscope system is varied as a series of one or more images are captured at each effective focal depth setting.

In some embodiments, the spatial resolution of the images provided by the compact optogenetic microscope system may range from about 0.1 μm to about 5 μm at the center of the field-of-view. In some embodiments, the spatial resolution may be at least 0.1 μm, at least 0.25 μm, at least 0.5 μm, at least 0.75 μm, at least 1 μm, at least 1.5 μm, at least 2 μm, at least 3 μm, at least 4 μm, or at least 5 μm at the center of the field-of-view. In some embodiments, the spatial resolution may be at most 5 μm, at most 4 μm, at most 3 μm, at most 2 μm, at most 1.5 μm, at most 1 μm, at most 0.75 μm, at most 0.5 μm, at most 0.25 μm, or at most 0.1 μm at the center of the field-of-view. Any of the lower and upper values described in this paragraph may be combined to form a range included within the disclosure, such as the spatial resolution may range from about 0.75 μm to about 2 μm at the center of the field-of-view. Those of skill in the art will recognize that spatial resolution may have any value within this range, e.g., about 1.6 μm, at the center of the field-of-view.

In some embodiments, the spatial resolution of the images provided by the compact optogenetic microscope system may vary across the field-of-view, and may range from about 0.1 μm to about 30 μm. In some embodiments, the minimum spatial resolution across the field-of-view may be at least 0.1 μm, at least 0.5 μm, at least 1 μm, at least 5 μm, at least 10 μm, at least 15 μm, at least 20 μm, at least 25 μm, or at least 30 μm. In some embodiments, the minimum spatial resolution may be at most 30 μm, at most 25 μm, at most 20 μm, at most 15 μm, at most 10 μm, at most 5 μm, at most 1 μm, at most 0.5 μm, or at most 0.1 μm. Any of the lower and upper values described in this paragraph may be combined to form a range included within the disclosure, such as the minimum spatial resolution may range from about 1 μm to about 20 μm. Those of skill in the art will recognize that minimum spatial resolution may have any value within this range, e.g., about 20 μm.

In some embodiments, one or more corrective optical elements (702 in FIG. 7) may be used to improve the spatial resolution of the images provided by the compact optogenetic microscope system across the entire field-of-view. In these embodiments, the minimum spatial resolution across the entire field-of-view may range from about 0.1 μm to about 5 μm. In some embodiments, the minimum spatial resolution across the entire field-of-view may be at least 0.1 μm, at least 0.25 μm, at least 0.5 μm, at least 0.75 μm, at least 1 μm, at least 1.5 μm, at least 2 μm, at least 3 μm, at least 4 μm, or at least 5 μm. In some embodiments, the minimum spatial resolution across the entire field-of-view may be at most 5 μm, at most 4 μm, at most 3 μm, at most 2 μm, at most 1.5 μm, at most 1 μm, at most 0.75 μm, at most 0.5 μm, at most 0.25 μm, or at most 0.1 μm. Any of the lower and upper values described in this paragraph may be combined to form a range included within the disclosure, such as the minimum spatial resolution across the entire field-of-view may range from about 0.75 μm to about 2 μm. Those of skill in the art will recognize that minimum spatial resolution may have any value within this range, e.g., about 1.6 μm.

In some embodiments, one or more adjustable lenses may be used to actively correct for chromatic aberrations. In some instances, the adjustable lens may be utilized to axially correct chromatic aberrations. For example, the chromatic aberration may be corrected or mitigated by changing a focal length of the adjustable lens as appropriate. For example, multi-color stimulation or imaging systems may experience chromatic aberration as different colors (e.g. different wavelengths) of light may be focused differently by an optical element such as a lens. Accordingly, for different wavelengths of light (or different wavelength ranges), it may be necessary to adjust a focal length of the adjustable lens in order to bring an image into focus or to focus stimulation light on the same sample plane as that used to image the sample or subject. In some embodiments, adjustments to the effective focal distance using an adjustable lens may be synchronized with capture of images by the image sensor.

Alternatively or in addition, the adjustable lens may be utilized in some embodiments to correct chromatic aberration in a lateral plane. For example, chromatic aberration in the lateral plane may be corrected or mitigated by tilting the adjustable lens to an appropriate tilt angle. In some instances, the adjustable lens may be tilted in a radial (i.e., where the lens is tilted from an angle of 0 degrees (aligned with the optical axis) in one direction to a specified angle (e.g., along the x-axis)) or circular pattern (i.e., where the lens is tilted to a fixed angle and then rotated around the optical axis a full 360 degrees) while a plurality of images is captured by the image sensor (e.g. using an image capture circuit that synchronizes the image capture process with tilting of the adjustable lens). Subsequently, the plurality of images captured in conjunction with the tilting and/or rotation of the lens may be processed to provide images that have been corrected for chromatic aberration. The plurality of captured images may comprise images captured at differing tilt angles. The differing tilt angles may refer to tilt angles that differ in magnitude, or that differ in a tilt direction about the optical axis. In some instances, the plurality of images may be captured at tilt angles having the same or similar magnitudes. Alternatively, the plurality of images may be captured at tilt angles having differing magnitudes. In some embodiments, dithering the tilt angle and direction of the adjustable lens (i.e., inducing random variations in tilt angle and direction) may be used to correct for chromatic aberration within a single image if the dithering is done at a sufficiently high frequency to provide coverage of the full field-of-view within the exposure time required to capture an image. In some embodiments, the tilt angle of the adjustable lens is dithered while a plurality of images is captured in a synchronized fashion.

In some embodiments, one or more processors may also be provided (e.g., integrated within the microscope housing, or as part of an external controller that communicates with the compact microscope system) to aid in correcting images for chromatic aberration. For example, the one or more processors may individually or collectively utilize a plurality of captured images to correct for or minimize chromatic aberration. The plurality of images may be the images captured with the adjustable lens tilted (e.g., in a circular or radial pattern) as described above. In some instances, the plurality of captured images may be combined, e.g., in post processing of the images, to produce a processed image. Combining or processing the plurality of images captured with differing tilt angles of the adjustable lens may reduce or eliminate chromatic aberration, e.g. in the lateral plane. The differing tilt angles may refer to tilt angles that differ in magnitude or in direction about the optical axis. In some instances, the plurality of captured images used to correct for chromatic aberration may be equal to or more than about 5 images, 10 images, 15 images, 20 images, 25 images, 30 images, 40 images, 50 images, 60 images, 80 images, 100 images, 150 images, 200 images, 250 images, 300 images, 400 images, or 500 images.

As mentioned, in some embodiments the capture of images by the image sensor may be synchronized with the tilting or dithering of the adjustable lens. For example, the adjustable lens may be tilted or dithered according to an image capture rate of the image sensor. Alternatively, the adjustable lens may be tilted or dithered at a rate greater than an image capture rate of the image sensor. Alternatively, the adjustable lens may dither or tilt at a rate lesser than an image capture rate of the sensor. The image capture circuit may capture images at a rate equal to about or more than 10 fps, 15 fps, 20 fps, 25 fps, 30 fps, 40 fps, 50 fps, 60 fps, 80 fps, 100 fps, 120 fps, 140 fps, 160 fps, 180 fps, 200 fps, 220 fps, 240 fps, 280 fps, 320 fps, 360 fps, 400 fps, or more. The adjustable lens may be adjusted (e.g., tilted, dither, etc) at a rate equal to or more than about 10 adjustments per second, 15 adjustments per second, 20 adjustments per second, 25 adjustments per second, 30 adjustments per second, 40 adjustments per second, 50 adjustments per second, 60 adjustments per second, 80 adjustments per second, 100 adjustments per second, 120 adjustments per second, 140 adjustments per second, 160 adjustments per second, 180 adjustments per second, 200 adjustments per second, 220 adjustments per second, 240 adjustments per second, 280 adjustments per second, 320 adjustments per second, 360 adjustments per second, 400 adjustments per second, or more.

In some instances, an adjustable lens may be especially useful for multi-color stimulation or multi-color imaging applications. As previously described herein, multi-color imaging may experience chromatic aberration or may capture out of focus images as different colors (e.g., wavelengths) of light can have different focal lengths when focused through an optical element such as a lens. Accordingly, for different wavelengths (e.g., different ranges of wavelengths), utilizing differing focal lengths may be appropriate or necessary to bring an image into focus. In some instances, the adjustable lens may be adjusted such that the focal length is appropriate to bring an image into focus for the different wavelengths of light. Optionally, one or more processors may be provided to vary a focal length of the imaging system (e.g., using an adjustable lens) such that captured images are always in focus for differing wavelengths of light.

In some instances, different optical arrangements or light sources emitting differing ranges of wavelengths of lights may be temporally multiplexed. In conjunction with the temporal multiplexing of the optical arrangements or light sources, an adjustable lens may be adjusted such that stimulation light is focused on the same sample or subject plane as that comprising the field-of view to be imaged. Also, in conjunction with the temporal multiplexing of the optical arrangements or light sources, an adjustable lens may be adjusted such that the imaging system is able to capture in-focus images for differing wavelengths of reflected, scattered, or emitted light. In some instances, the adjustable lens' focal length may be adjusted substantially simultaneously with the temporal multiplexing of the optical arrangements or light sources in order to bring captured images into focus. Alternatively, the adjustable lens' focal length may be adjusted substantially sequentially with the temporal multiplexing of the optical arrangements or light sources in order to bring captured images into focus. In some instances, one or more processors may be provided to ensure that the focal length of the imaging system or adjustable lens is adjusted appropriately according to light (e.g., excitation light) produced by the optical arrangements or light sources to bring captured images into focus. Alternatively or in addition, the one or more processors may be provided to ensure that the focal length of the imaging system or adjustable lens is adjusted appropriately according to light (e.g., emission light) produced by the samples to bring captured images into focus. Additionally, the adjustable lens may be tilted and/or dithered to mitigate or correct for chromatic aberrations as referred to above.

As discussed above, the compact optogenetic microscope may be used to study both human subjects or animal subjects. In those embodiments comprising one or more adjustable lenses, the adjustable lenses may be used, for example, to bring the imaging light and stimulation light into the same or different focal planes and/or fields-of-view, or for example, to correct for chromatic aberration within the field-of-view. A non-limiting example of a method for using the compact optogenetic microscope to simultaneously stimulate and image tissue within a subject may comprise: a) providing an optical system according to any of the embodiments disclosed herein; b) providing a subject comprising the tissue to be stimulated and imaged; c) mounting or implanting the optical system of step (a) on or within the subject; and d) generating one or more images of the tissue before, during, or after directing stimulation light to the tissue of said subject in a time-modulated or spatially-modulated manner. The compact optogenetic microscopes disclosed herein may be used, for example, for modulating presynaptic inputs of neural tissue while imaging postsynaptic cells, imaging and modulating the same population of cells, or imaging and modulating different populations within the same field-of-view. In some embodiments, animal subjects may include rodents (e.g., mice, rats, rabbits, guinea pigs, gerbils, hamsters), simians, canines, felines, avines, insects, or any other type of animal. In some embodiments, the microscope may be mounted on, or inserted into, a living subject (or a non-living subject) and used for pre-clinical or clinical research. In some embodiments, the microscope may be used for clinical diagnostic or therapeutic applications. In some embodiments, the compact optogenetic microscope may be used in conjunction with light-activated ion channels to deliver a spatio-temporal pattern of optical stimulation that, when processed by the neural tissue of the brain, triggers a specific effect in the subject. Examples of specific effects that may be triggered in the subject by delivery of a spatio-temporal pattern of optical stimulation include, but are not limited to, changes in appetite/feeding behavior, invoking of fear/avoidance behavior, reward-seeking behavior, enhancement or suppression of motor activity in general, and alteration of sleep patterns.

Implantable Microscope Systems

In some embodiments of the compact optogenetic microscope system disclosed herein, the system may be configured as a partially or fully-implantable device (i.e., one in which the device does not break the skin barrier). In these embodiments, the microscope system, or components thereof (e.g., one or more individual optical illumination probes, optical stimulation probes, optical imaging probes, or any combination thereof) may be enclosed in a hermetically-sealed, biocompatible housing, e.g., a housing having an outer surface fabricated from a biocompatible material. Non-limiting examples of suitable materials for fabricating the biocompatible housing (or outer surface thereof) may include various metals (e.g., stainless steels, cobalt-based alloys, titanium, and titanium-based alloys), polymers (e.g., polypropylene, high-density polyethylene, polymethylmethacrylate, and silicone), ceramics (e.g., zirconium dioxide), composite materials, or combinations thereof.

In these implantable embodiments, the microscope system may further comprise a wireless transmitter/receiver (or wireless adapter, e.g., a radio frequency or optical wireless link) that communicates with an external controller and enables wireless data and power transmission between the external controller and the implanted device. In some embodiments, the wireless transmitter/receiver provides for both data read and data write communication (separately and/or simultaneously). Wireless data transmission rates in these embodiments may range from about 1 Mbit/s to about 7 Gbit/s. In some embodiments, the wireless data transmission rate may be at least about 1 Mbit/s, at least about 5 Mbit/s, at least about 10 Mbit/s, at least about 50 Mbit/s, at least about 100 Mbit/s, at least about 200 Mbit/s, at least about 300 Mbit/s, at least about 400 Mbit/s, at least about 500 Mbit/s, at least about 600 Mbit/s, at least about 700 Mbit/s, at least about 800 Mbit/s, at least about 900 Mbit/s, at least about 1 Gbit/s, at least about 2 Gbit/s, at least about 3 Gbit/s, at least about 4 Gbit/s, at least about 5 Gbit/s, at least about 6 Gbit/s, or at least about 7 Gbit/s.

The implantable microscope systems disclosed herein may comprise optical designs, optical performance characteristics, and physical features as described for other embodiments of the compact optogenetic microscope systems disclosed herein. Application of the implantable microscope systems include optical stimulation of genetically-modified tissue in a subject, wherein the tissue has been genetically modified to incorporate light-driven ion channels and/or fluorescent calcium indicators, or other fluorescent ion indicators, and wherein the implanted device is configured to deliver s spatially and/or temporally modulated sequence of stimulation light pulses to neurons within the illumination field and/or field-of-view of the device so as to stimulate a selected neuron or set of neurons that are processed by the subject to trigger a therapeutic response. In some embodiments, e.g., those in which the subject's tissue has been genetically-modified to include fluorescent calcium indicators or other fluorescent ion indicators, the implanted device may be configured to both deliver the spatially and/or temporally modulated sequence of stimulation light pulses, and to image the response induced in the targeted neurons (i.e., the neurons that are stimulated by the stimulation light pulses). In some embodiments, the imaged response in the targeted neurons, or in neurons adjacent to or in close proximity to the targeted neurons, is used via a feedback loop to modify the spatial and/or temporal pattern of stimulation light pulses. Examples of potential applications for the implanted devices of the present disclosure include optogenetic inducement of atrial fibrillation in test subjects, optogenetic stimulation of cardiac muscle tissue in cardiac patients, optogenetic stimulation of retinal neurons in vision-loss patients, and optogenetic stimulation of the vagus nerve in epilepsy patients. Other examples of potential applications include, but are not limited to, stimulation to induce alterations in sleep, appetite, drug-dependence, gambling, or other habitual behaviors, suppression of tremor in Parkinson's patients, and restoration of normal movement in other movement disorders.

Control Systems

Figure 5:
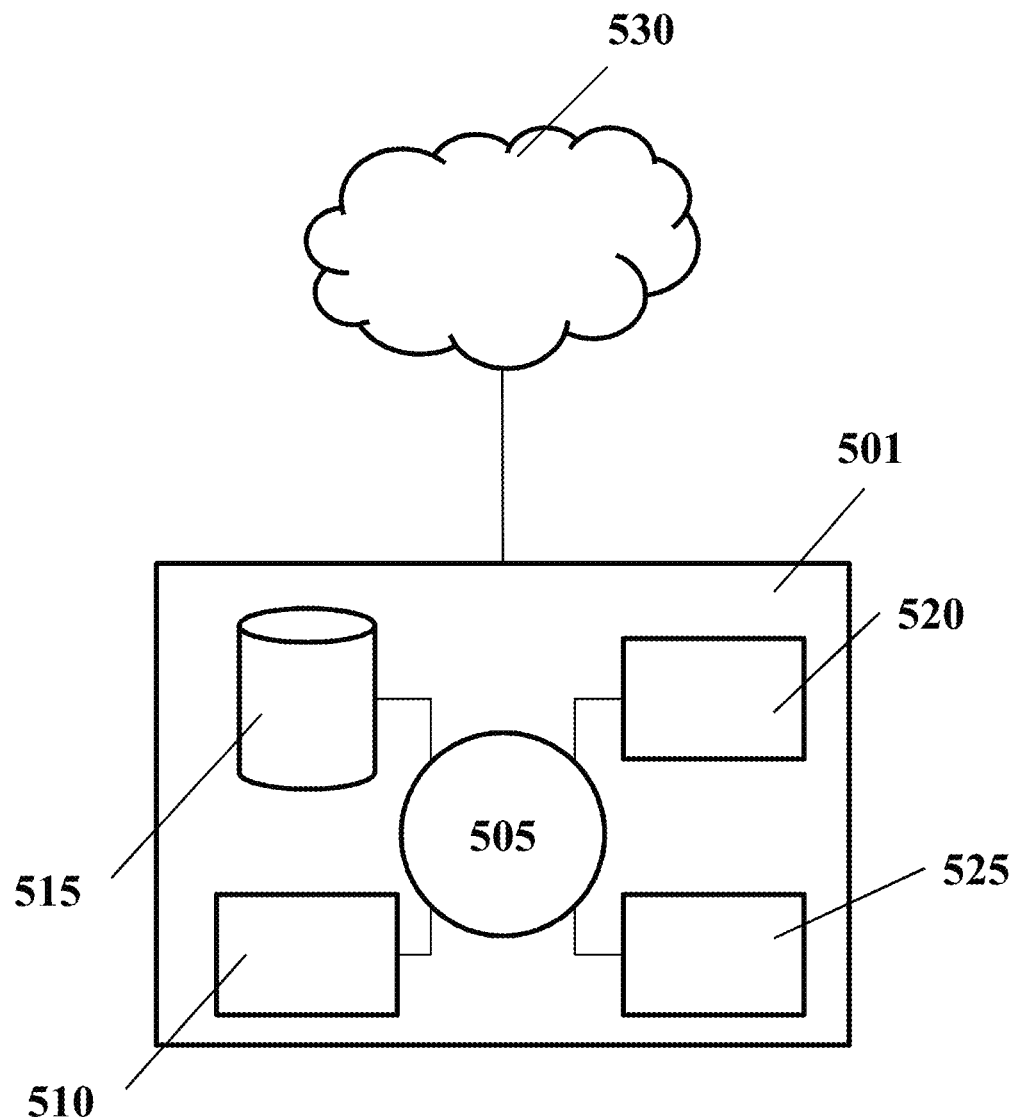
FIG. 5 shows a computer system configured to control the microscope system.

The present disclosure provides computer control systems that are programmed to implement methods of the disclosure. FIG. 5 shows a computer system 501 that is programmed or otherwise configured to control a stimulation light source incident on a sample. The computer system can be configured to identify regions of a sample that comprise one or more objects of interest for stimulation by the stimulation light source. The computer system can regulate various aspects of the stimulation light source, such as, for example, the intensity, location of incident light on the sample in the field-of-view of the microscope system, and/or the duration of the illumination of the sample by the stimulation light source.

The computer system includes a central processing unit (CPU, also "processor" and "computer processor" herein) 505, which can be a single core or multi core processor, or a plurality of processors for parallel processing. The computer system also includes memory or memory location 510 (e.g., random-access memory, read-only memory, flash memory), electronic storage unit 515 (e.g., hard disk), communication interface 520 (e.g., network adapter) for communicating with one or more other systems, and peripheral devices 525, such as cache, other memory, data storage and/or electronic display adapters. The memory, storage unit, interface and peripheral devices are in communication with the CPU 505 through a communication bus (solid lines), such as a motherboard. The storage unit can be a data storage unit (or data repository) for storing data. The computer system 501 can be operatively coupled to a computer network ("network") 530 with the aid of the communication interface 520. The network can be the Internet, an internet and/or extranet, or an intranet and/or extranet that is in communication with the Internet. The network in some cases is a telecommunication and/or data network. The network 530 can include one or more computer servers, which can enable distributed computing, such as cloud computing. The network 530, in some cases with the aid of the computer system, can implement a peer-to-peer network, which may enable devices coupled to the computer system to behave as a client or a server.

The CPU 505 can execute a sequence of machine-readable instructions, which can be embodied in a program or software. The instructions may be stored in a memory location, such as the memory 510. Examples of operations performed by the CPU can include fetch, decode, execute, and writeback.

The CPU can be part of a circuit, such as an integrated circuit. One or more other components of the system can be included in the circuit. In some cases, the circuit is an Application Specific Integrated Circuit (ASIC).

The storage unit can store files, such as drivers, libraries and saved programs. The storage unit can store user data, e.g., user preferences and user programs. The computer system in some cases can include one or more additional data storage units that are external to the computer system, such as located on a remote server that is in communication with the computer system through an intranet or the Internet.

The computer system can communicate with one or more remote computer systems through the network 530. For instance, the computer system can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system via the network.

Methods as described herein can be implemented by way of machine (e.g., computer processor) executable code stored on an electronic storage location of the computer system, such as, for example, on the memory or electronic storage unit. The machine executable or machine readable code can be provided in the form of software. During use, the code can be executed by the processor 505. In some cases, the code can be retrieved from the storage unit and stored on the memory for ready access by the processor. In some situations, the electronic storage unit can be precluded, and machine-executable instructions are stored on memory.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computer system, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system can include or be in communication with an electronic display that comprises a user interface (UI) for providing, for example, a display of an image captured by the microscope system. The image can be generated by the imaging light. The image can comprise the currently field-of-view of the microscope system. The image can comprise one or more objects of interest for stimulation by the stimulation light source. Examples of UI's include, without limitation, a graphical user interface (GUI) and web-based user interface.

Figure 8A:
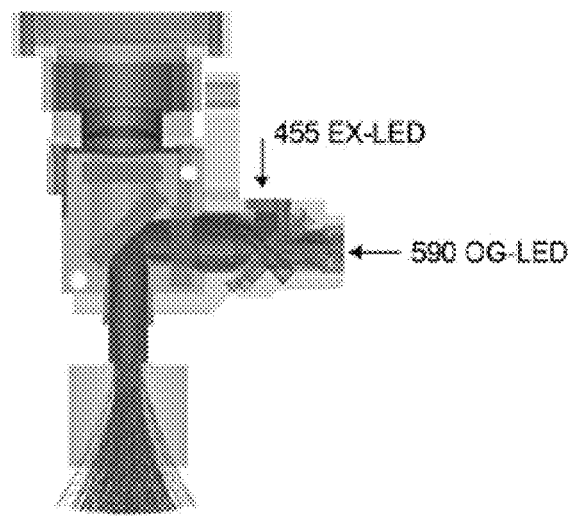
FIGS. 8A-B illustrates two non-limiting examples of configurations for a compact optogenetics microscope.
Figure 8B:
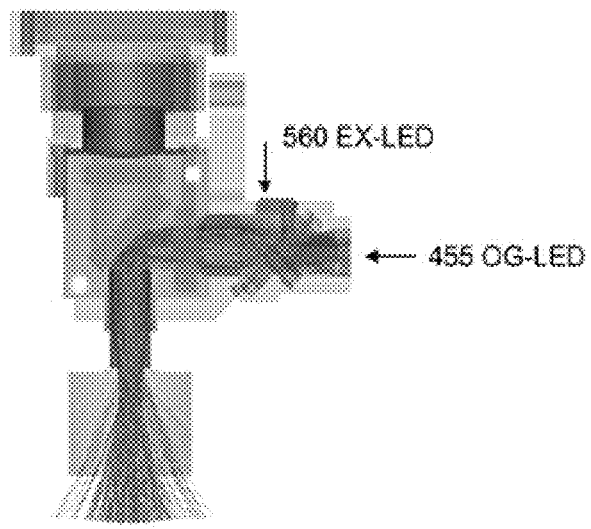

Example—Simultaneous Calcium Imaging and Optogenetic Manipulation in Freely Behaving Mice Optogenetics has revolutionized systems neuroscience by providing a tool to causally link distinct neurocircuit activity behavior. In addition, advances in calcium indicators and imaging techniques have led to important discoveries on how various internal and external stimuli drive the activity of distinct neuronal populations. Here, we describe two non-limiting examples of lightweight integrated microscopes (FIGS. 8A-B, which illustrate compact optogenetic microscopes having different fluorescence excitation and photostimulation wavelengths) that allow for simultaneous and sequential cellular resolution imaging and optical manipulation within the same field-of-view in freely behaving mice.

FIGS. 9A-C illustrates non-limiting examples of different imaging applications for a compact optogenetics microscope system. These integrated microscopes allow for several different imaging and optogenetic applications within the same field-of-view, including modulating presynaptic inputs while imaging postsynaptic cells (FIG. 9A), imaging and modulating the same population of cells (FIG. 9B), and imaging and modulating different populations within the same field-of-view (FIG. 9C).

Figure 10A:
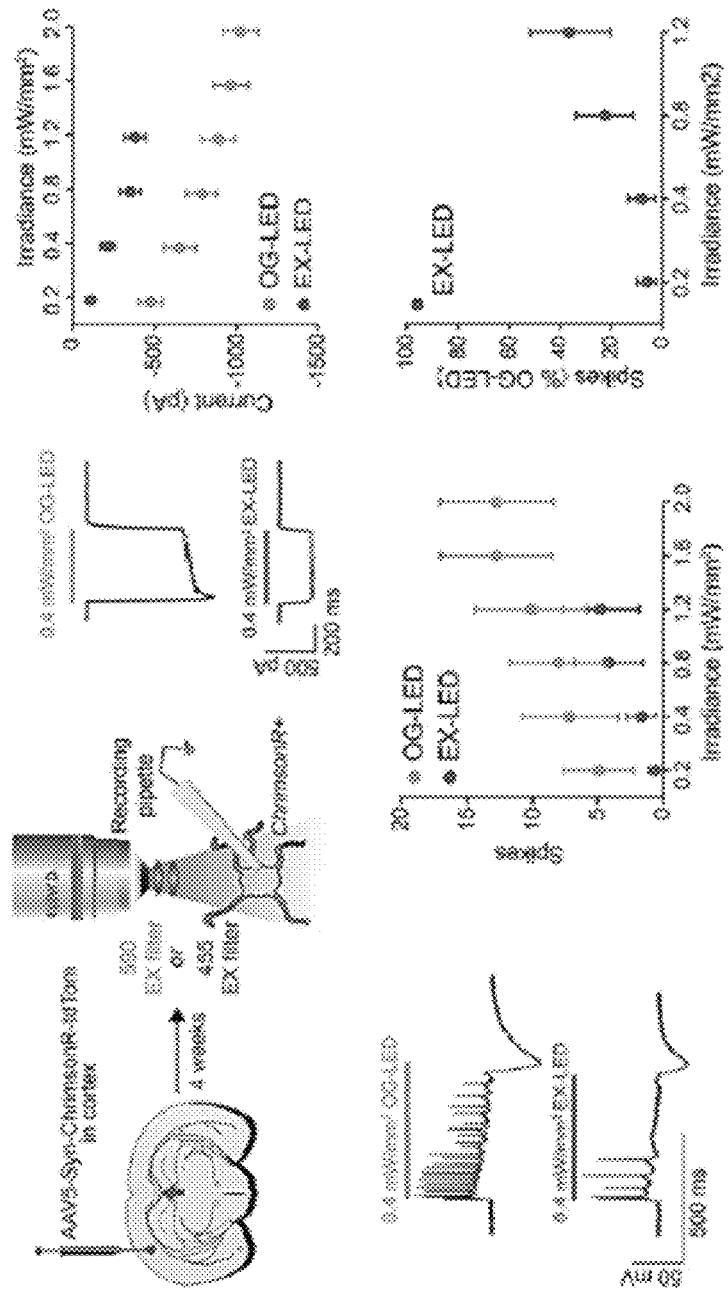
FIG. 10A-D shows examples of data for in vitro characterization of biological crosstalk with excitatory opsins.
Figure 10B:
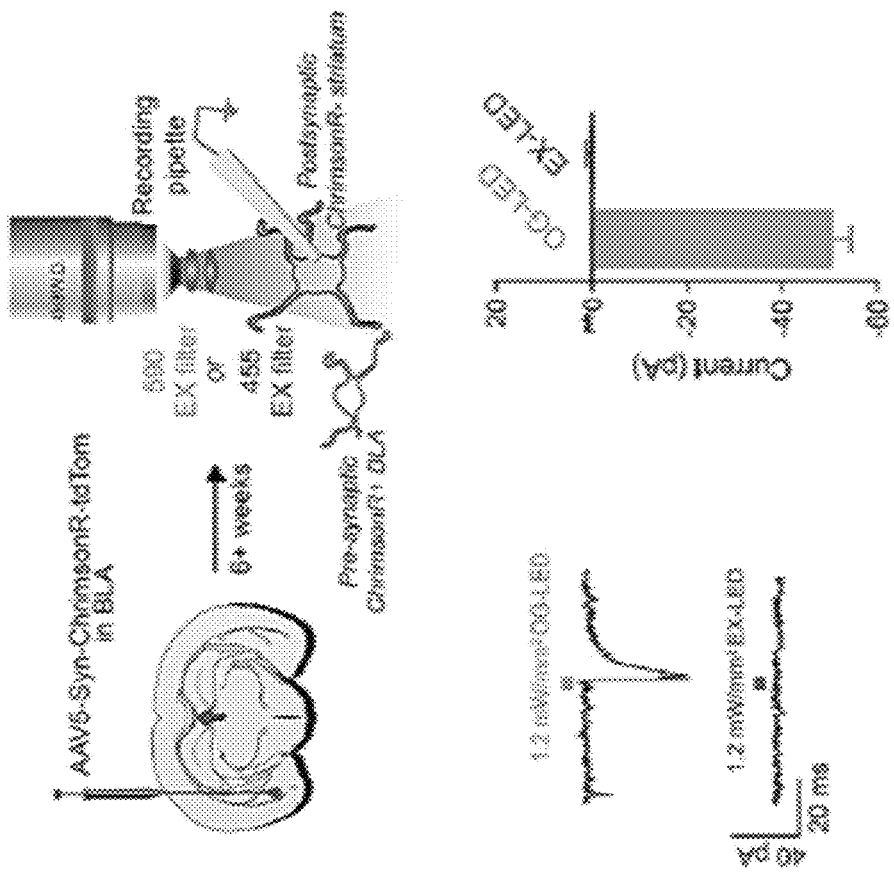
Figure 10C:
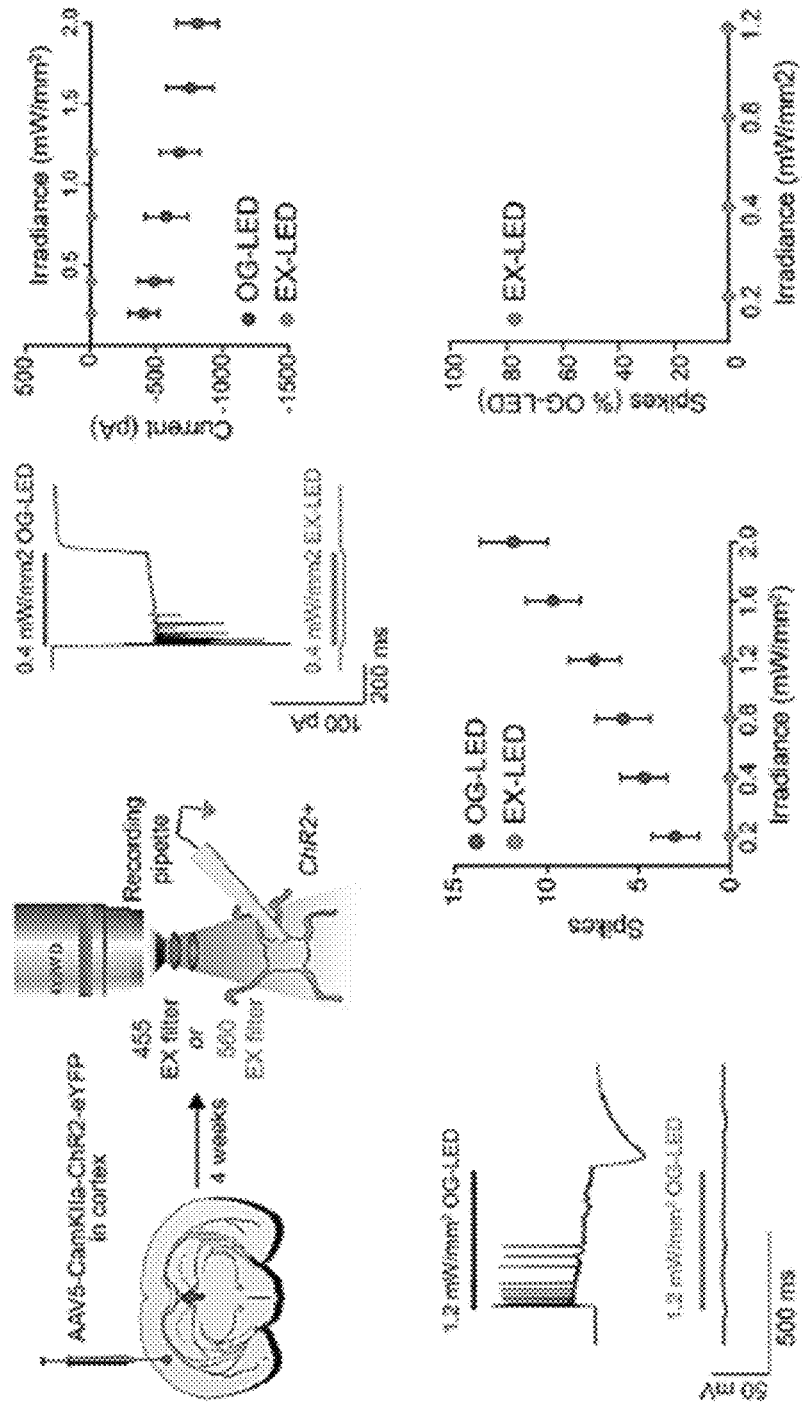
Figure 10D:
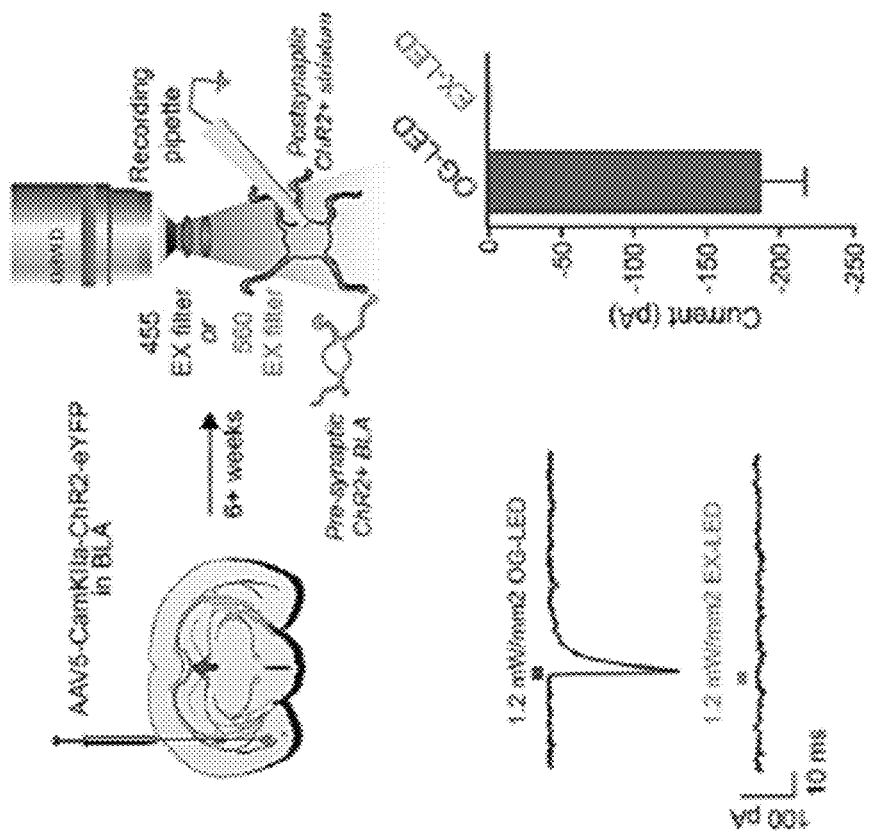

FIG. 10A-D shows examples of data for in vitro characterization of biological crosstalk with excitatory opsins. To determine if the excitation LED light source (EX-LED) activates excitatory opsins, mice were injected with either MVS-Syn-ChrimsonR-tdTom (FIG. 10A, upper left) or MVS-CamKIa-ChR2-eYFP (FIG. 10C, upper left) into the cortex. At 4+ weeks following injection, we performed whole-cell patch-clamp electrophysiology in cortical brain slices (FIGS. 10A and 10C, upper right). We found that blue light filtered with the nVista-OPTO 455EX excitation filter significantly activated ChrimsonR in somas (FIG. 10A, lower left and lower right), but showed no significant activation of ChrimsonR in terminals (FIG. 10B, lower left and lower right) We found that green light filtered with the nVista-OPTO 560EX excitation filter did not significantly activate ChR2 in somas or terminals (FIG. 10C, lower right, and 10D, lower left and lower right).

Figure 11A:
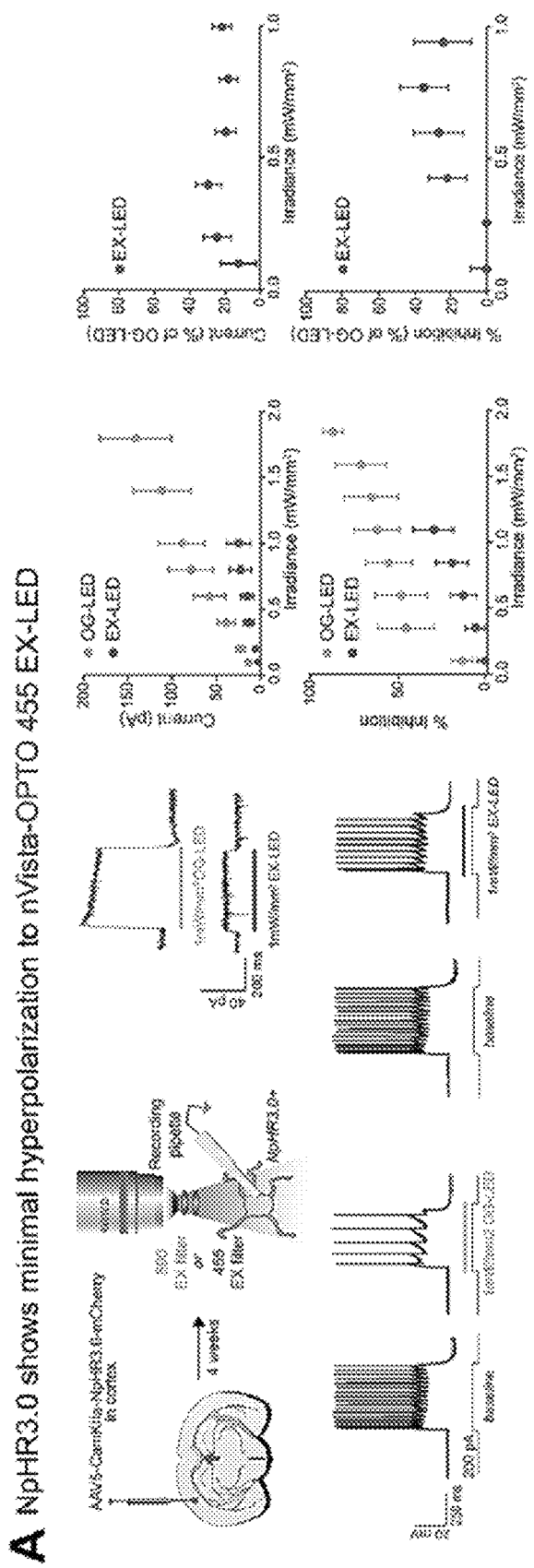
FIG. 11A-B shows examples of data for in vitro characterization of biological crosstalk with inhibitory opsins.
Figure 11B:
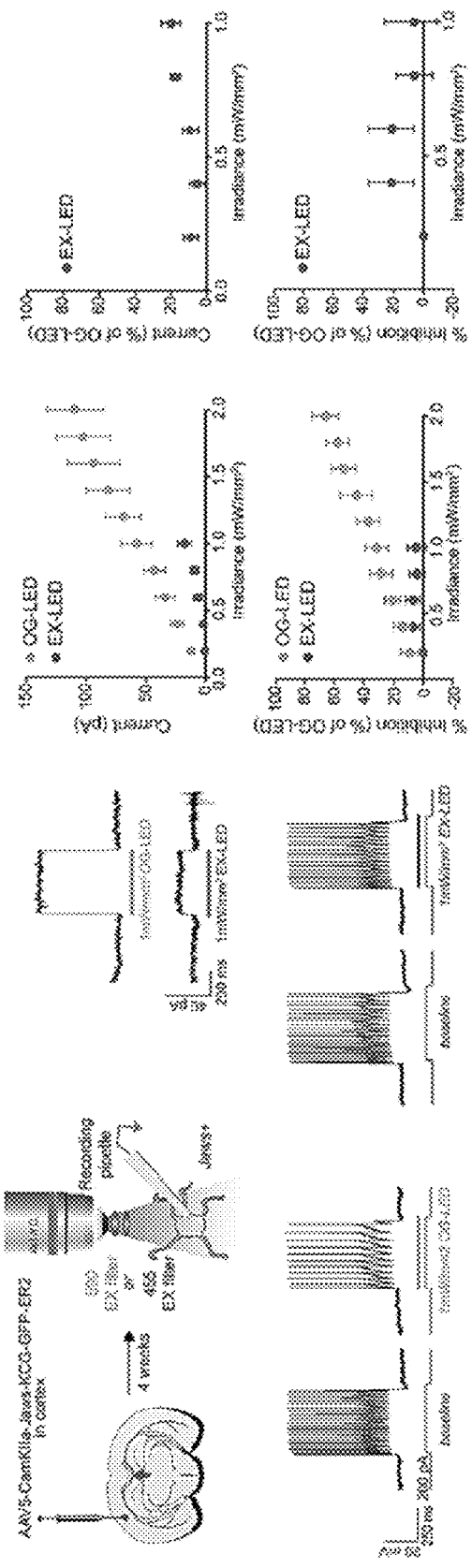

FIG. 11A-B shows examples of data for in vitro characterization of biological crosstalk with inhibitory opsins. To determine if the EX-LED activated inhibitory opsins, mice were injected with either MV5-CamKIIa-NpHR3.0-mCherry (FIG. 11A, upper left) or MV5-CamKII-Jaws-KGC-GFP-ER2 (FIG. 11B, upper left) into the cortex. At 4+ weeks following injection, we performed whole-cell patch-clamp electrophysiology in cortical brain slices. We found that blue light filtered with the nVista-OPTO 455EX excitation filter resulted in some activation of NpHR3.0 (FIG.

11A) and Jaws (FIG. 11B). However, at the lower irradiances used for imaging, this crosstalk was minimal.

FIGS. 12A-B show examples of data for in vivo characterization of biological crosstalk. We determined if the 1) OG-LED provided enough power to cause the intended behavioral response and 2) if the EX-LED altered behavior. For nVista-OPTO 455EX, mice were injected with AAV5-syn-ChrimsonR-tdTom into the LHb and a 6 mm lens was inserted above the RMTg (FIG. 12A, upper) For nVista-OPTO 560EX, mice were injected with AAV5-CamKIIa-ChR2-eYFP and a 7 mm lens was implanted above the BNST (FIG. 12B, upper). In a real time place preference assay, mice did not show any preference or avoidance to a chamber paired with exposure to EX-LED from the nVista-OPTO 455EX. Mice showed a real time place aversion to a side of a chamber paired with exposure to 60 Hz OG-LED from the nVista-OPTO 455EX (FIG. 12A, lower). In a feeding assay, mice did not show any changes in feeding during exposure to EX-LED from the nVisla-OPTO 560EX. Mice showed increased feeding during exposure to 20 Hz OG-LED from the nVista-OPTO 560EX (FIG. 12B, lower).

FIGS. 13A-B show examples of data for in vivo characterization of mechanical crosstalk. To determine if the OG-LED excited autofluorescence in the brain tissue, endoscope, or microscope, naive mice (not expressing opsin or indicator), were implanted with 4 mm lenses above the hippocampus or dorsal striatum. Imaging sessions consisted of OG-LED off for 30 s, OG-LED on for 30 s, repeated 3 times. EX-LED was off the entire time. The nVista-OPTO 455EX OG-LED did not activate any autofluorescence in the brain tissue, endoscope or microscope, as evident by no significant change in fluorescent counts between OG-LED on and OG-LED off (FIG. 13A). The nVista-OPTO 560EX OG-LED significantly activated autofluorescence in the microscope, endoscope, and brain tissue, as evident by significantly more counts of fluorescence between OG-LED on and OG-LED off (FIG. 13B).

Figure 14:
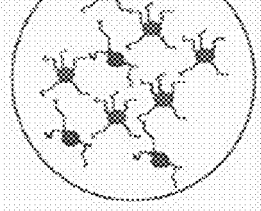
FIG. 14 shows non-limiting examples of suitable opsin/indicator combinations for use with the disclosed compact optogenetic microscope systems.

FIG. 14 shows non-limiting examples of suitable opsin/indicator combinations for use with the disclosed compact optogenetic microscope systems. ChR2 shows minimal in vitro and in vivo crosstalk. RGECO and RCaMP are currently being validated in vivo. Simultaneous GCaMP imaging with somal red-shifted opsin manipulation will require further engineering of red-shifted opsins, such that they are not excited somally by blue light.

Figure 15:
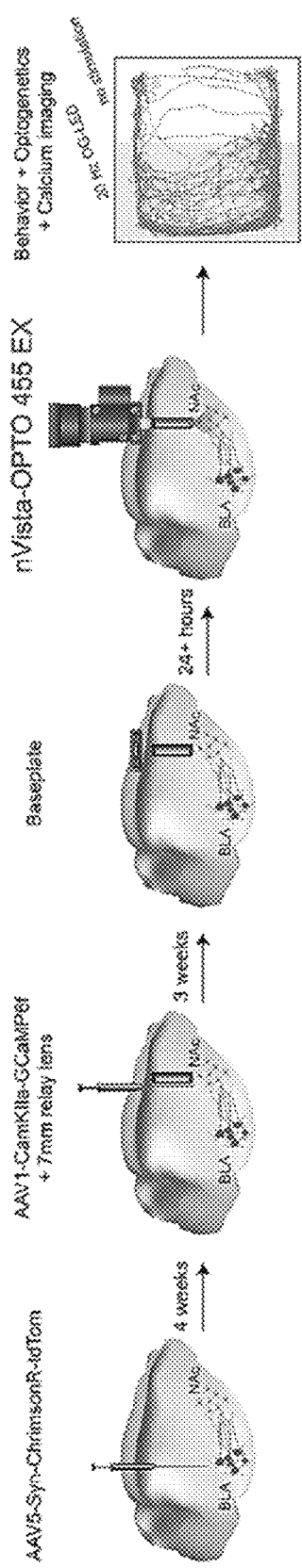
FIG. 15 illustrates one non-limiting example of the steps taken in setting up and performing an optogenetic study using the disclosed compact optogenetic microscope systems.

FIG. 15 illustrates one non-limiting example of the steps taken in setting up and performing an optogenetic study using the disclosed compact optogenetic microscope systems. Mice were injected with AAVS-Syn-ChrimsonR-tdTom into the BLA. 4 weeks later mice were injected with AAV1-CamKIIa-GCaMP6f into the NAc. In the same surgery, mice were implanted with a 7 mm relay lens above the NAc. Three weeks later mice were implanted with a baseplate that allows for attachment of the nVista-OPTO microscopes. Mice were given access to an open chamber for 20 minutes. If the mouse made a cross into the stimulation-paired side of the chamber, it received is of 20 Hz OG-LED every Ss. If the mouse crossed into the no stimulation-paired side, it received no OG-LED stimulation. Imaging via the EX-LED occurred during the entire 20 minutes. As expected, we found that mice spent more time in the stimulation-paired side of the chamber, demonstrating that the BLA-Io-NAc circuit is rewarding. In addition, we observed an increase in calcium activity that coincided with delivery of the OG-LED.

We have developed two new compact optogenetic microscope systems that allow for imaging and optogenetic manipulation in the same field-of-view in freely behaving animals. We have conducted in vitro and in vivo biological feasibility studies to determine which opsin/indicator combinations are feasible with each microscope. Finally, we have demonstrated simultaneous optogenetic manipulation and calcium imaging in a freely behaving mouse. Combining optogenetics and calcium imaging in an integrated light weight microscope may allow researchers to begin to establish a causal link between neural circuit dynamics and behavior.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A microscope system for simultaneous imaging and stimulation of tissue within a subject, the microscope system comprising:
   a) an optical assembly that includes:
      i. an illumination optical path comprising one or more light-emitting elements and configured to direct imaging light to the tissue within a specified field-of-view;
      ii. a stimulation optical path comprising one or more light-emitting elements and configured to direct stimulation light to the tissue within said field-of-view, to the tissue outside of said field-of-view, or to the tissue partially within said field-of-view;
      iii. an imaging optical path comprising one or more image sensors and configured to receive light reflected, scattered, or emitted by the tissue to generate an image of the tissue within said field-of-view;
   b) a corrective optical element optically cooperated with an element of the optical assembly to achieve a spatial resolution of better than 2 µm over the entirety of the specified field-of-view; and
   a baseplate is configured to be mounted on the subject in a fixed position and to receive the optical assembly, thereby aligning the optical assembly relative to the tissue within the subject upon attachment to the baseplate, and wherein the optical assembly is removable from the baseplate.

2. The microscope system of claim 1, wherein the specified field-of-view is about 1 mm×1 mm.

3. The microscope system of claim 1, wherein the specified field-of-view is about 2 mm×2 mm.

4. The microscope system of claim 1, wherein the specified field-of-view is about 4 mm×4 mm.

5. The microscope system of claim 1, wherein the imaging light is fluorescence excitation light.

6. The microscope system of claim 5, wherein the fluorescence excitation light has a wavelength within a wavelength range of 400 nm to 500 nm, and the stimulation light has a wavelength within a wavelength range of 500 nm and 800 nm.

7. The microscope system of claim 5, wherein the fluorescence excitation light has a wavelength within a wavelength range of 500 nm to 650 nm, and the stimulation light has a wavelength within a wavelength range of 350 nm and 560 nm.

8. The microscope system of claim 1, wherein the optical assembly is configured to acquire images with a spatial resolution of better than 2 µm at a center of the field-of-view.

9. The microscope system of claim 1, wherein the optical assembly further comprises one or more deformable lenses configured to adjust a corresponding focal depth of the imaging optical path, the stimulation optical path, or both.

10. The microscope system of claim 9, wherein the illumination optical path, stimulation optical path, and imaging optical path share at least one deformable lens of said one or more deformable lenses.

11. The microscope system of claim 9, wherein the one or more deformable lenses are configured to adjust the corresponding focal depth of the imaging optical path, the stimulation optical path, or both over a range of about 300 µm without loss of spatial resolution.

12. The microscope system of claim 9, wherein the one or more deformable lenses are selected from the group consisting of liquid lenses, liquid crystal lenses, piezo-actuated tunable lenses, and any combination thereof.

13. The microscope system of claim 9, wherein the one or more deformable lenses are configured so that the imaging optical path and the stimulation optical path direct light to the same focal plane.

14. The microscope system of claim 9, wherein the optical assembly is configured to acquire images over a tissue volume of about 1 mm×1 mm×300 µm.

15. The microscope system of claim 1, wherein the stimulation optical path is further configured to direct the stimulation light to the tissue in a user-defined spatial pattern.

16. The microscope system of claim 15, wherein the user-defined spatial pattern has a spatial resolution of better than 5 µm at a corresponding focal plane.

17. The microscope system of claim 1, further comprising a processor and a memory device, wherein the processor is configured to execute a series of software-encoded instructions stored in the memory device.

18. The microscope system of claim 17, wherein the software-encoded instructions include instructions for: (i) modulating intensity of the imaging light in a time-dependent manner or a spatially-dependent manner, (ii) modulating intensity of the stimulation light in a time-dependent manner or a spatially-dependent manner, (iii) varying a corresponding focal depth of the imaging optical path, the stimulation optical path, or both in a time-dependent manner, and (iv) capturing one or more images of the tissue within the specified field-of-view at specified times, or any combination thereof.

19. A microscope system for simultaneous imaging and stimulation of tissue within a subject, the microscope system comprising:
  a) an optical assembly that includes
    i. an illumination optical path comprising one or more light-emitting elements and configured to direct imaging light to the tissue within a specified field-of-view;
    ii. a stimulation optical path comprising one or more light-emitting elements and configured to direct stimulation light to the tissue within said field-of-view, to tissue outside of said field-of-view, or to the tissue partially within said field-of-view;
    iii. an imaging optical path comprising one or more image sensors and configured to receive light reflected, scattered, or emitted by the tissue to generate an image of the tissue within said field-of-view; and
    iv. one or more deformable lenses configured to adjust a corresponding focal depth of the imaging optical path,
  the stimulation optical path, or both over a range of about 300 µm without loss of spatial resolution; and
  b). a baseplate configured to be mounted on the subject in a fixed position and to receive the optical assembly, thereby aligning the optical assembly relative to the tissue within the subject upon attachment to the baseplate, and wherein the optical assembly is removable from the baseplate.

20. The microscope system of claim 9, wherein the one or more deformable lenses are configured so that the imaging optical path and the stimulation optical path direct light to the same focal plane.

* * * * *